(12) United States Patent
Kruse et al.

(10) Patent No.: US 8,729,101 B2
(45) Date of Patent: *May 20, 2014

(54) 1H-IMIDAZOLE DERIVATIVE HAVING $CB_1$ AGONISTIC, $CB_1$ PARTIAL AGONISTIC OR $CB_1$ ANTAGONISTIC ACTIVITY

(75) Inventors: Cornelis G. Kruse, Weesp (NL); Josephus H. M. Lange, Weesp (NL); Arnoldus H. J. Herremans, Weesp (NL); Herman H. Van Stuivenberg, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 795 days.

This patent is subject to a terminal disclaimer.

(21) Appl. No.: 12/203,113

(22) Filed: Sep. 2, 2008

(65) Prior Publication Data
US 2009/0181949 A1 Jul. 16, 2009

Related U.S. Application Data

(63) Continuation of application No. 10/490,019, filed as application No. PCT/EP02/10434 on Sep. 17, 2002, now abandoned.

(30) Foreign Application Priority Data
Sep. 21, 2001 (EP) .................................. 01203851

(51) Int. Cl.
*A61K 31/454* (2006.01)
*C07D 401/02* (2006.01)

(52) U.S. Cl.
USPC ..... 514/326; 546/210; 546/274.1; 548/311.1; 548/333.5; 514/341; 514/397; 514/399

(58) Field of Classification Search
USPC .................. 514/326, 341, 397, 399; 546/210, 546/274.1; 548/311.1, 333.5
See application file for complete search history.

(56) References Cited

U.S. PATENT DOCUMENTS

| | | | |
|---|---|---|---|
| 4,813,998 A | 3/1989 | Van Lommen et al. | |
| 5,616,601 A | 4/1997 | Khanna et al. | |
| 5,624,941 A | 4/1997 | Barth et al. | |
| 6,432,984 B1 | 8/2002 | Barth et al. | |
| 6,492,516 B1 * | 12/2002 | Liverton et al. | 544/324 |
| 6,960,601 B2 * | 11/2005 | Smith et al. | 514/326 |
| 7,109,216 B2 * | 9/2006 | Kruse et al. | 514/318 |
| 7,524,867 B2 * | 4/2009 | Lange et al. | 514/326 |
| 2004/0248956 A1 | 12/2004 | Hagmann et al. | |

FOREIGN PATENT DOCUMENTS

| | | | | |
|---|---|---|---|---|
| DE | 140966 | * | 4/1980 | A01N 43/48 |
| EP | 0 576 357 A1 | | 6/1993 | |
| WO | WO 00/46209 A1 | | 8/2000 | |
| WO | WO 00/63204 A2 | | 10/2000 | |
| WO | WO 00/69848 A1 | | 11/2000 | |
| WO | WO 01/70700 A1 | | 9/2001 | |
| WO | WO 02/076949 A1 | | 10/2002 | |
| WO | WO 03/040107 A1 | | 5/2003 | |
| WO | WO 03/063781 A2 | | 8/2003 | |

OTHER PUBLICATIONS

Ueda, T. et al.: A novel ring transformation of 5-acylaminouracils and 5-acylaminopyrimidin-4-ones into imidazoles. Tetrahed. Lett. vol. 29, pp. 4607-4610, 1988.*

Li, Z. F. et al., "Facile Synthesis of Amidines Via Intermolecular Reductive Coupling of Nitriles with Azobenzene Promoted by Samarium Diiodide", Chemical Abstracts, vol. 133, No. 18, 1 page, (Oct. 30, 2000).

Pertwee, R. G., "Pharmacology of Cannabinoid Receptor Ligands", Current Medicinal Chemistry, vol. 6, No. 8, pp. 635-664, (1999).

Ueda, T. et al., "A Novel Ring Transformation of 5-Acylaminouracils and 5-Acylamino-Pyrimidin-4(3H)-Ones Into Imidazoles", Tetrahedron Letters, vol. 29, No. 36, pp. 4607-4610, (1988).

Kudo, N. et al., "Synthesis and Herbicidal Activity of 1,5-Diarylpyrazole Derivatives", Chem. Pharm. Bull., vol. 47, No. 6, pp. 857-868, (Jun. 1999).

Khanna, I. K. et al., "1,2-Diarylimidazoles as Potent, Cyclooxygenase-2 Selective, and Orally Active Antiinflammatory Agents", J. Med. Chem., vol. 40, No. 11, pp. 1634-1647, (1997).

Khanna, I. K. et al., "Selective Cyclooxygenase-2 Inhibitors: Heteroaryl Modified 1,2-Diarylimidazoles Are Potent, Orally Active Antiinflammatory Agents", J. Med. Chem., vol. 43, No. 16, pp. 3168-3185, (2000).

Thomas, B. F. et al., "Comparative Receptor Binding Analyses of Cannabinoid Agonists and Antagonists", The Journal of Pharmacology and Experimental Therapeutics, vol. 285, No. 1, pp. 285-292, (1998).

(Continued)

*Primary Examiner* — Charanjit Aulakh
(74) *Attorney, Agent, or Firm* — Finnegan, Henderson, Farabow, Garrett & Dunner

(57) ABSTRACT

The present invention relates to a group of novel 1H-imidazole derivatives, to methods for the preparation of these compounds, and to pharmaceutical compositions containing one or more of these compounds as an active component. These 1H-imidazole derivatives are potent cannabinoid-$CB_1$ receptor agonists, partial agonists or antagonists, useful for the treatment of psychiatric and neurological disorders, as well as and other diseases involving cannabinoid neurotransmission. The compounds have the general formula (I), wherein R and $R_1$-$R_4$ have the meanings given in the specification.

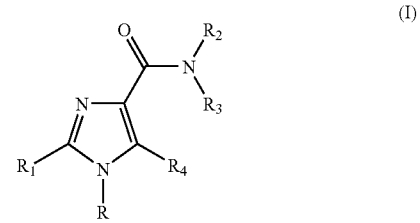

6 Claims, No Drawings

(56) References Cited

OTHER PUBLICATIONS

Dyck, B. et al., "Potent Imidazole and Triazole $CB_1$ Receptor Antagonists Related to SR141716", Bioorganic & Medicinal Chemistry Letters 14, pp. 1151-1154, (2004).

Lange, J.H.M. et al., "Synthesis, Biological Properties, and Molecular Modeling Investigatgions of Novel 3, 4-Diarylpyrazolines as Potent and Selective $CB_1$ Cannabinoid Receptor Antagonists", J. Med. Chem., 2004, 47, pp. 627-643.

Lan, R. et al., "Structure—Activity Relationships of Pyrazole Derivatives as Cannabinoid Receptor Antagonists", J. Med. Chem., 1999, 42, pp. 769-776.

Nakamura-Palacios, E.M. et al., "The Pharmacology of SR 141716A: A Review", CNS Drug Reviews, vol. 5, No. 1 pp. 43-58, 1999.

Reddy, D.B. et al.,"A concise and efficient method for 2-pyrazolines.", Indian Journal of Chemistry, vol. 34B, Sep. 1995, pp. 811-815.

Panchal, J.M. and Desai, K.R., "Synthesis and Antibacterial Activity of 2-Pyrazolines and Their Related Compounds", Asian Journal of Chemistry, vol. 12. No. 2 (2000), pp. 609-611.

Goya, P., et al., "Modulation of peristalsis by cannabinoid $CB_1$ ligands in the isolated guinea-pig ileum", Exp. Opin. Ther. Patents (2000) 10(10), pp. 1529-1538.

Consroe, P., "Brain Cannabinoid Systems as Targets for the Therapy of Neurological Disorders", Neurobiology of Disease, 5, pp. 534-551, (1998).

Deroche-Gamonet, V. et al, "SR141716, a CB1 receptor antangonist, decreases the sensitivity to the reinforcing effects of electrical brain stimulation in rats",Psychopharmacology, (2001), 157, pp. 254-259.

Pertwee, R., "Neuropharmacology and therapeutic potential of cannabinoids", Addiction Biology, (2000), 5, 37-46.

Izzo, A. et al., "Modulation of peristalsis by cannabinoid $CB_1$ receptor ligands in the isolated guinea pig ileum", British Journal of Pharmacology, (2000), 129, pp. 984-990.

Pertwee, R., "Cannabinoids and the gastrointestinal tract", Gut 2001, 48, pp. 859-867.

Consroe, P., "Cannabinoid Systems as Targets for the Therapy of Neurological Disorders", Neurobiology of Disease, 5, pp. 534-551, (1998).

Barnouin et al., "Blockade of cannabinoid (CB1) receptors by SR 141716 selectively antagonizes drug-induced reinstatement of exploratory behavior in gerbils," Psychopharmacology (1999) 144: 144-150.

Haller et al., "The effects of genetic and pharmacological blockade of the CB1 cannabinoid receptor on anxiety," Eur. J. Neuroscience 2002, vol. 16, pp. 1395-1398, 2002.

Mansbach et al., "Effects on the cannabinoid CB1 receptor antagonist SR141716A on the behavior of pigeons and rats," Psychopharmacology (1996) 124: 315-322.

\* cited by examiner

1H-IMIDAZOLE DERIVATIVE HAVING CB₁, AGONISTIC, CB₁ PARTIAL AGONISTIC OR CB₁ ANTAGNISTIC ACTIVITY

The present application is a continuation of U.S. patent application Ser. No. 10/490,019, filed Mar. 19, 2004, which is a national stage entry of International Application No. PCT/EP02/10434, filed Sep. 17, 2002, which claims priority from European Patent Application No. 01203851.9, filed Sep. 21, 2001, the content of each of which is incorporated herein by reference.

The present invention relates to a group of novel 1H-imidazole derivatives, to methods for the preparation of these compounds, and to pharmaceutical compositions containing one or more of these compounds as an active component. These 1H-imidazole derivatives are potent cannabinoid-CB₁ receptor agonists, partial agonists or antagonists, useful for the treatment of psychiatric and neurological disorders, as well as and other diseases involving cannabinoid neurotransmission.

Cannabinoids are present in the Indian hemp *Cannabis sativa* and have been used as medicinal agents for centuries (Mechoulam, R. and Feigenbaum, J. J. *Prog. Med. Chem.* 1987, 24, 159). However, only within the past ten years the research in the cannabinoid area has revealed pivotal information on cannabinoid receptors and their (endogenous) agonists and antagonists. The discovery and the subsequent cloning of two different subtypes of cannabinoid receptors (CB₁ and CB₂) stimulated the search for novel cannabinoid receptor antagonists (Munro, S. et al., *Nature* 1993, 365, 61. Matsuda, L. A. and Bonner, T. I. *Cannabinoid Receptors*, Pertwee, R. G. Ed. 1995, 117, Academic Press, London). In addition, pharmaceutical companies became interested in the development of cannabinoid drugs for the treatment of diseases connected with disorders of the cannabinoid system (Consroe, P. *Neurobiology of Disease* 1998, 5, 534. Pop, E. *Curr. Opin. In CPNS Investigational Drugs* 1999, 1, 587. Greenberg, D. A. *Drug News Perspect.* 1999, 12, 458. Pertwee, R. G., *Progress in Neurobiology* 2001, 63, 569). Hitherto, several CB₁ receptor antagonists are known. Sanofi disclosed their diarylpyrazole congeners as selective CB₁ receptor antagonists. A representative example is SR-141716A (Dutta, A. K. et al., *Med. Chem. Res.* 1994, 5, 54. Lan, R. et al., *J. Med. Chem.* 1999, 42, 769. Nakamura-Palacios, E. M. et al., *CNS Drug Rev.* 1999, 5, 43). CP-272871 is a pyrazole derivative, like SR141716A, but less potent and less CB₁ receptor subtype-selective than SR141716A (Meschler, J. P. et al., *Biochem. Pharmacol.* 2000, 60, 1315). Aminoalkylindoles have been dis-closed as CB₁ receptor antagonists. A representative example is Iodopravadoline (AM-630), which was introduced in 1995. AM-630 is a moderately active CB₁ receptor antagonist, in some assays behaving as a weak partial agonist (Hosohata, K. et al, *Life Sc.* 1997, 61, PL115). Researchers from Eli Lilly described aryl-aroyl substituted benzofurans as selective CB₁ receptor antagonists (e.g. LY-320135) (Felder, C. C. et al., *J. Pharmacol Exp. Ther.* 1998, 284, 291). 3-Alkyl-5,5'-diphenylimidazolidine-diones were described as cannabinoid receptor ligands, which were indicated to be cannabinoid antagonists (Kanyonyo, M. et al., *Biorg. Med. Chem. Lett.* 1999, 9, 2233). Aventis Pharma claimed diarylmethyleneazetidine analogs as CB₁ receptor antagonists (Mignani, S. et al., Patent FR 2783246, 2000; *Chem. Abstr.* 2000, 132, 236982). Tricyclic pyrazoles were claimed by Sanofi-Synthelabo as CB₁ antagonists (Barth, F. et al. Patent WO 0132663, 2001; *Chem. Abstr.* 2001, 134, 340504). Interestingly, many CB₁ receptor antagonists have been reported to behave as inverse agonists in vitro (Landsman, R. S. et al., *Eur. J. Pharmacol.* 1997, 334, R1). Pyrazole cannabinoids have also been reported as CB₁ receptor partial agonists showing in vivo cannabimimetic effects (Wiley, J. L. et al., *J. Pharmacol. Exp. Ther.* 2001, 296, 1013). A number of classes of CB₁ receptor agonists are known such as for example the classical cannabinoids (e.g. Δ⁹-THC), non-classical cannabinoids, aminoalkylindoles and eicosanoids (e.g. anandamide). Reviews provide a nice overview of the cannabinoid research area (Mechoulam, R. et al., *Prog. Med. Chem.* 1998, 35, 199. Lambert, D. M. *Curr. Med. Chem.* 1999, 6, 635. Mechoulam, R. et al., *Eur. J. Pharmacol.* 1998, 359, 1. Williamson, E. M. and Evans, F. J. *Drugs* 2000, 60, 1303. Pertwee, R. G. *Addiction Biology* 2000, 5, 37. Robson, P. *Br. J. Psychiatry* 2001, 178, 107. Pertwee, R. G. *Prog. Neurobiol.* 2001, 63, 569. Goya, P. and Jagerovic, N. *Exp. Opin. Ther. Patents* 2000, 10, 1529. Pertwee, R. G. *Gut* 2001, 48, 859).

It has now surprisingly been found that the novel 1H-imidazole derivatives of the formula (I), prodrugs thereof and salts thereof, are potent agonists, partial agonists or antagonists on cannabinoid-CB₁ receptors

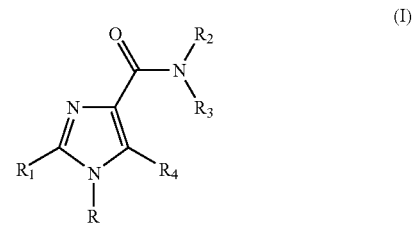

(I)

wherein

R represents phenyl, thienyl, 2-pyridinyl, 3-pyridinyl, 4-pyridinyl, pyrimidinyl, pyrazinyl, pyridazinyl or triazinyl, which groups may be substituted with 1, 2, 3 or 4 substituents Y, which can be the same or different, from the group $C_{1-3}$-alkyl or alkoxy, hydroxy, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkoxycarbonyl, carboxyl, cyano, carbamoyl and acetyl, or R represents naphtyl, with the proviso that when R is 4-pyridinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, which $C_{1-4}$ alkyl group may be substituted with 1-3 fluoro atoms or with a bromo, chloro, iodo, cyano or hydroxy group, $R_1$ represents phenyl or pyridinyl, which groups may be substituted with 1-4 substituents Y, which can be the same or different, wherein Y has the above mentioned meaning, or $R_1$ represents pyrimidinyl, pyrazinyl, pyridazinyl or triazinyl, which groups may be substituted with 1-2 substituents Y, which can be the same or different or $R_1$ represents a five-membered aromatic heterocyclic ring having one or two heteroatoms from the group (N, O, S), which heteroatoms can be the same or different, which five-membered aromatic heterocyclic ring may be substituted with 1-2 substituents Y, which can be the same or different or $R_1$ represents naphtyl, $R_2$ represents H, branched or unbranched $C_{1-8}$ alkyl, $C_{3-8}$ cycloalkyl, $C_{3-8}$ alkenyl, $C_{5-8}$ cycloalkenyl which groups may contain a sulfur, oxygen or nitrogen atom, $R_3$ represents branched or unbranched $C_{2-8}$ alkyl, $C_{1-8}$ alkoxy, $C_{5-8}$ cycloalkyloxy, $C_{3-8}$ cycloalkyl, $C_{5-10}$ bicycloalkyl, $C_{6\text{-}10}$ tricycloalkyl, $C_{3\text{-}8}$ alkenyl, $C_{5\text{-}8}$ cycloalkenyl, which groups may optionally contain one or more heteroatoms from the group (O, N, S) and which groups may be substituted with a hydroxy group or 1-2 $C_{1\text{-}3}$ alkyl groups or 1-3 fluoro atoms, or $R_3$ represents a benzyl or phenethyl group which aromatic rings may be substituted with 1-5 substituents Z, which can be the same or different, from the group $C_{1\text{-}3}$-alkyl or alkoxy, hydroxy, halogen, trifluoromethyl, trifluoromethylthio, trifluoromethoxy, nitro, amino, mono- or dialkyl ($C_{1\text{-}2}$)-amino, mono- or dialkyl ($C_{1\text{-}2}$)-amido, ($C_{1\text{-}3}$)-alkylsulfonyl, dimethyl-sulfamido, $C_{1\text{-}3}$-alkoxycarbonyl, carboxyl, trifluoromethylsulfonyl, cyano, carbamoyl, sulfamoyl and acetyl, or $R_3$ represents a phenyl or pyridinyl group, which groups are substituted with 1-4 substituents Z, wherein Z has the meaning as indicated above, or $R_3$ represents a pyridinyl group, or $R_3$ represents a phenyl group, with the proviso that $R_4$ represents a halogen atom or a cyano, carbamoyl, formyl, acetyl, trifluoroacetyl, fluoroacetyl, propionyl, sulfamoyl, methanesulfonyl, methylsulfanyl or $C_{1\text{-}4}$ alkyl group, which $C_{1\text{-}4}$ alkyl group may be substituted with 1-3 fluoro atoms or with a bromo, chloro, iodo, cyano or hydroxy group, or $R_3$ represents a group $NR_5R_6$ with the proviso that $R_2$ represents a hydrogen atom or a methyl group, wherein $R_5$ and $R_6$ are the same or different and represent branched or unbranched $C_{1\text{-}4}$ alkyl, or $R_5$ and $R_6$—together with the nitrogen atom to which they are bonded—form a saturated or unsaturated, monocyclic or bicyclic heterocyclic group having 4 to 10 ring atoms which heterocyclic group contains one or two heteroatoms from the group (N, O, S), which heteroatoms can be the same or different, which heterocyclic group may be substituted with a $C_{1\text{-}3}$ alkyl group or a hydroxy group, or $R_2$ and $R_3$— together with the nitrogen atom to which they are bonded—form a saturated or unsaturated heterocyclic group having 4 to 10 ring atoms which heterocyclic group contains one or two heteroatoms from the group (N, O, S), which heteroatoms can be the same or different, which heterocyclic group may be substituted with a $C_{1\text{-}3}$ alkyl group or a hydroxy group, $R_4$ represents a hydrogen or halogen atom or a cyano, carbamoyl, formyl, acetyl, trifluoroacetyl, fluoroacetyl, propionyl, sulfamoyl, methanesulfonyl, methylsulfanyl or branched or unbranched $C_{1\text{-}4}$ alkyl group, which $C_{1\text{-}4}$ alkyl group may be substituted with 1-3 fluoro atoms or with a bromo, chloro, iodo, cyano or a hydroxy group, Due to the potent $CB_1$ agonistic, partial agonistic or antagonistic activity the compounds according to the invention are suitable for use in the treatment of psychiatric disorders such as psychosis, anxiety, depression, attention deficits, memory disorders, cognitive disorders, appetite disorders, obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, diabetes, cancer, emesis, nausea, gastrointestinal disorders, gastric ulcers, diarrhoea and cardiovascular disorders.

The affinity of the compounds of the invention for cannabinoid $CB_1$ receptors was determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

The cannabinoid $CB_1$ antagonistic activity of compounds of the invention was determined by functional studies using CHO cells in which human cannabinoid $CB_1$ receptors are stably expressed. Adenylyl cyclase was stimulated using forskolin and measured by quantifying the amount of accumulated cyclic AMP. Concomitant activation of $CB_1$ receptors by $CB_1$ receptor agonists (e.g. CP-55,940 or (R)-WIN-55, 212-2) can attenuate the forskolin-induced accumulation of cAMP in a concentration-dependent manner. This $CB_1$ receptor-mediated response can be antagonized by $CB_1$ receptor antagonists such as the compounds of the invention.

Cannabinoid agonistic of partial agonistic activity of compounds of the invention can be determined according to published methods, such as assessment of in vivo cannabimimetic effects (Wiley, J. L. et al., *J. Pharmacol. Exp. Ther.* 2001, 296, 1013).

The invention relates both to racemates, mixtures of diastereomers and the individual stereoisomers of the compounds having formula (I).

The compounds of the invention can be brought into forms suitable for administration by means of usual processes using auxiliary substances and/or liquid or solid carrier materials.

Suitable synthetic routes for the compounds of the invention are the following:

Synthetic Route A

Step 1: ester hydrolysis of a compound having formula (II) wherein $R_7$ represents a branched or unbranched alkyl group ($C_{1\text{-}4}$) or benzyl group

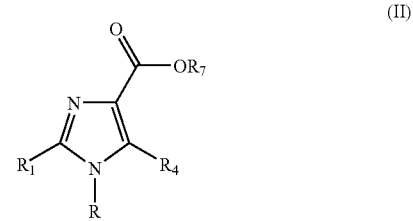

(II)

This reaction gives a compound having formula (III)

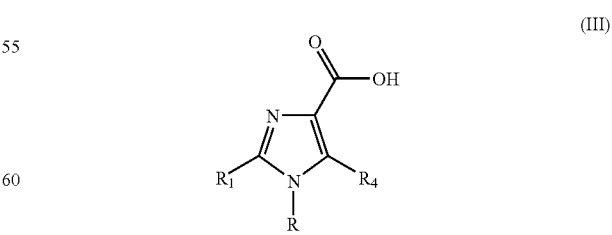

(III)

wherein R, $R_1$ and $R_4$ have the meanings as described above.

Intermediates having formula (II), wherein $R_7$ represents a branched or unbranched alkyl group ($C_{1\text{-}4}$) or benzyl group can be obtained according to methods known, for example:

a) I. K. Khanna et al., *J. Med. Chem.* 2000, 43, 3168-3185
b) N. Kudo et al., *Chem. Pharm. Bull.* 1999, 47, 857-868
c) K. Tsuji et al., *Chem. Pharm. Bull.* 1997, 45, 987-995
d) I. K. Khanna et al., *J. Med. Chem.* 1997, 40, 1634-1647
e) M. Guillemet et al., *Tetrahedron Lett.* 1995, 36, 547-548

Step 2: reaction of a compound having formula (III) with a compound having formula $R_2R_3NH$ wherein $R_2$ and $R_3$ have the meanings as described above via activating and coupling methods such as formation of an active ester, or in the presence of a coupling reagent such as DCC, HBTU, BOP or similar reagents. This reaction gives a desired 1H-imidazole derivative having formula (I).

(For more information on activating and coupling methods see: M. Bodanszky and A. Bodanszky: *The Practice of Peptide Synthesis*, Springer-Verlag, New York, 1994; ISBN: 0-387-57505-7).

Alternatively, a compound having formula (III) is reacted with a halogenating agent, for example thionyl chloride ($SOCl_2$). This reaction gives the corresponding carbonyl chloride (IV).

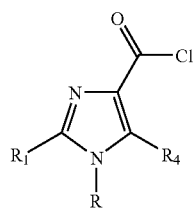

(IV)

Reaction of a compound having formula (IV) with a compound having formula $R_2R_3NH$ wherein $R_2$ and $R_3$ have the meanings as described above, yields a 1H-imidazole derivative having formula (I). This reaction is preferably carried out in the presence of an organic base such as for example diisopropylethylamine (DIPEA) or triethylamine.

Alternatively, a compound having formula (II) is reacted in an amidation reaction with a compound having formula $R_2R_3NH$ wherein $R_2$ and $R_3$ have the meanings as described above to give a 1H-imidazole derivative having formula (I).

Synthetic Route B

Reaction of a compound having formula (II), wherein $R_4$ represents hydrogen and wherein $R$, $R_1$ and $R_7$ have the meanings as described above for compound (II), with a compound having general formula $R_4'$-X, wherein X represents a leaving group and $R_4'$ represents a $C_{1-4}$ alkyl group, which alkyl group may be substituted with 1-3 fluoro atoms or wherein $R_4'$ represents a cyano, formyl, acetyl, trifluoroacetyl, fluoroacetyl, methylsulfanyl or propionyl moiety, or a halogen atom. This reaction is carried out in the presence of a strong non-nucleophilic base such as lithium diisopropylamide (LDA), preferably under anhydrous conditions in an inert organic solvent, for example tetrahydrofuran, and yields a compound having formula (II)

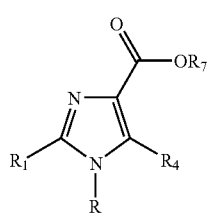

(II)

wherein R, $R_1$ and $R_7$ have the meanings as described hereinabove and $R_4$ represents a $C_{1-4}$ alkyl group, which alkyl group may be substituted with 1-3 fluoro atoms or wherein $R_4$ represents a cyano, formyl, acetyl, trifluoroacetyl, fluoroacetyl, methylsulfanyl or propionyl group, or a halogen atom.

Compounds of general formula (II) which have been obtained according to synthesis route B can be converted to compounds of general formula (I) analogously to the procedures described in synthesis route A, step 1 of route A or step 2 of route A (see above).

Synthetic Route C

Compounds Having Formula (II)

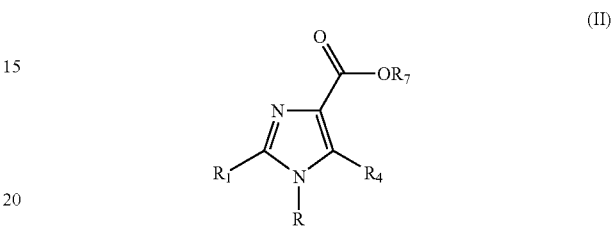

(II)

wherein $R_4$ represents a branched or unbranched $C_{1-4}$ alkyl group, which $C_{1-4}$ alkyl group may be substituted with 1-3 fluoro substituents and wherein R, $R_1$ have the meanings given above and $R_7$ represents a branched or unbranched alkyl group ($C_{1-4}$) or benzyl group can be synthesized by reacting a compound having formula (V) or its tautomer

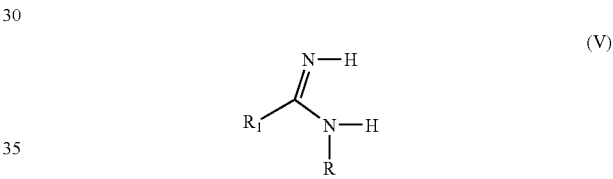

(V)

wherein R and $R_1$ have the meanings given above, with a compound having formula (VI)

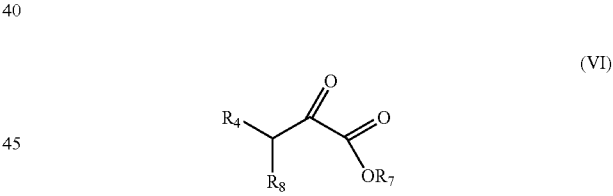

(VI)

wherein $R_4$ represents a branched or unbranched $C_{1-4}$ alkyl group, which $C_{1-4}$ alkyl group may be substituted with 1-3 fluoro atoms and $R_8$ represents a leaving group, for example a bromo substituent, and $R_7$ represents a branched or unbranched alkyl group ($C_{1-4}$) or benzyl group. The reaction is preferably carried out in an organic solvent, for example in 2-propanol or in N-methyl-2-pyrrolidinone (NMP). The addition of an acid like trifluoroacetic acid (TFA) during the reaction may enhance the formation of the compounds having formula (II).

(For more information on the leaving group concept see: M. B. Smith and J. March: *Advanced organic chemistry*, p. 275, 5$^{th}$ ed., (2001) John Wiley & Sons, New York, ISBN: 0-471-58589-0).

Compounds of general formula (II) which have been obtained according to synthesis route C can be converted to compounds of general formula (I) analogously to the procedures described in synthesis route A, step 1 of route A or step 2 of route A (see above).

Compounds of the invention having formula (VI) can be obtained according to methods known, for example: P. Seifert et al., *Helv. Chim. Acta,* 1950, 33, 725.

Synthetic Route D

Reaction of a Compound Having Formula (II)

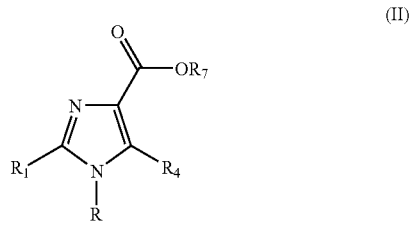

(II)

wherein $R_4$ represents a methyl group and R, $R_1$ have the meanings given above and $R_7$ represents a branched or unbranched alkyl group ($C_{1-4}$) or benzyl group with a regioselective brominating compound such as N-bromo-succinimide (NBS) in an organic solvent such as $CCl_4$ in the presence of a free-radical initiator like dibenzoyl peroxide gives a compound of formula (VII)

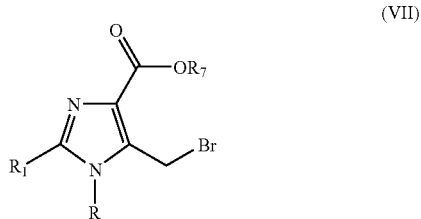

(VII)

wherein R, $R_1$ and $R_7$ have the meanings given above. Reaction of a compound having formula (VII) (analogous to the method described in Mathews, W. B. et al., *J. Label. Compds. Radiopharm.,* 1999, 42, 589) with for example KCl, KI, KF or KCN gives a compound of formula (VIII)

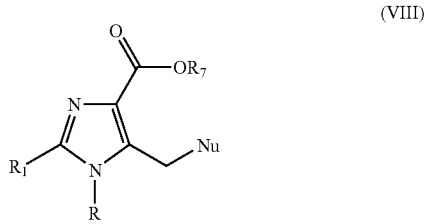

(VIII)

wherein R, $R_1$ and $R_7$ have the meanings given hereinabove and Nu represents a chloro, iodo, fluoro or cyano group. The reaction is preferably carried out in the presence of a weak base like $NaHCO_3$ or in the presence of a crown ether or a cryptand. (For more information on crown ethers and cryptands see: M. B. Smith and J. March: *Advanced organic chemistry,* p. 105, $5^{th}$ ed., (2001) John Wiley & Sons, New York, ISBN: 0-471-58589-0).

Compounds of general formula (VII) or (VIII) which have been obtained according to synthesis route D can be converted to compounds of general formula (I) analogously to the procedures described in synthesis route A, step 1 of route A, or step 2 of route A (see above).

EXAMPLE 1

Part A: To a 1M solution of sodium bis(trimethylsilyl) amide in THF (70 mL) is added dropwise a solution of 4-chloroaniline (8.86 gram, 69.5 mmol) in anhydrous THF in a nitrogen atmosphere. After the mixture is stirred for 20 minutes a solution of 2,4-dichlorobenzonitrile (12 gram, 70 mmol) in THF is added. The resulting mixture is stirred overnight, poured into ice-water (400 mL) and extracted with dichloromethane, dried over $Na_2SO_4$ and concentrated in vacuo to give a yellow oil (15.7 gram). Crystallisation from a dichloromethane/heptane mixture, and subsequent washing with methyl-t-butyl ether gives N-(4-chlorophenyl)-2,4-dichlorobenzenecarboxamidine (8.66 gram, 42% yield) as a yellow solid. Melting point (MP): 93-95° C.

Analogously was prepared:
N-(4-bromophenyl)-2,4-dichlorobenzenecarboxamidine.
MP: 117-119° C.

Part B: A mixture of N-(4-chlorophenyl)-2,4-dichlorobenzenecarboxamidine (2.00 gram, 6.68 mmol), ethyl 3-bromo-2-oxopropanoate (2.65 gram, 13.6 mmol) and $NaHCO_3$ (1.12 gram, 13.3 mmol) in 2-propanol is stirred at reflux temperature for 20 hours. After cooling to room temperature the mixture is concentrated in vacuo and the residue suspended in dichloromethane, washed with water (3×50 mL) and brine (3×50 mL). The aqueous layers are extracted with dichloromethane. The combined organic layers are dried over $Na_2SO_4$ and concentrated in vacuo to afford crude brown product (2.0 gram). This product is further purified by column chromatography (silicagel, heptane/EtOAc=90/10 (v/v)) to yield ethyl 1-(4-chlorophenyl)-2-(2,4-dichlorophenyl)-1H-imidazole-4-carboxylate (0.759 gram, 29% yield) as a yellow oil which slowly solidifies on standing. Melting point: 150-152° C.; MS: 395 ($MH^+$). $^1$H-NMR (400 MHz, $CDCl_3$): δ 7.91 (s, 1H), 7.49 (dd, J=8 Hz, J=2 Hz, 1H), 7.29-7.36 (m, 4H), 7.07 (dt, J=8 Hz, J=2 Hz, 2H), 4.44 (q, J=7 Hz, 2H), 1.42 (t, J=7 Hz, 3H).

Part C: Ethyl 1-(4-chlorophenyl)-2-(2,4-dichlorophenyl)-1H-imidazole-4-carboxylate (0.810 gram, 2.06 mmol) and LiOH (0.173 g, 7.20 mmol) are dissolved in a $H_2O$/THF (20 mL/20 mL) mixture and stirred at 50° C. for 16 hours. The mixture is concentrated in vacuo to give 1-(4-chlorophenyl)-2-(2,4-dichlorophenyl)-1H-imidazole-4-carboxylic acid. Thionyl chloride (60 mL) is added and the mixture is heated at reflux temperature for 1 hour and concentrated in vacuo to give crude 1-(4-chlorophenyl)-2-(2,4-dichlorophenyl)-1H-imidazole-4-carbonyl chloride.

Part D: Crude 1-(4-chlorophenyl)-2-(2,4-dichlorophenyl)-1H-imidazole-4-carbonyl chloride (919 mg, ~2.39 mmol), 1-aminopiperidine (0.469 g, 4.69 mmol) and triethylamine (0.363 g, 3.59 mmol) are dissolved in dichloromethane and stirred for one hour at room temperature. The mixture is washed with a saturated aqueous $NaHCO_3$ solution (3×20 mL), dried over $Na_2SO_4$ and concentrated in vacuo and further purified by column chromatography (ethyl acetate, silicagel) to give 1-(4-chlorophenyl)-2-(2,4-dichlorophenyl)-N-(piperidin-1-yl)-1H-imidazole-4-carboxamide (356 mg, 26% yield (based on ethyl 1-(4-chlorophenyl)-2-(2,4-dichlorophenyl)-1H-imidazole-4-carboxylate). Mass Spectrometry (MS): 449.

Analogously were prepared:
2. 1-(4-Chlorophenyl)-2-(2,4-dichlorophenyl)-N-(pyrrolidin-1-yl)-1H-imidazole-4-carboxamide; MS: 435.
3. N-(t-Butoxy)-1-(4-chlorophenyl)-2-(2,4-dichlorophenyl)-1H-imidazole-4-carboxamide; MS: 438.
4. 1-(4-Chlorophenyl)-2-(2,4-dichlorophenyl)-N-phenyl-1H-imidazole-4-carboxamide; MS: 442.

5. 1-(4-Chlorophenyl)-N-cyclohexyl-2-(2,4-dichlorophenyl)-1H-imidazole-4-carboxamide; MS: 448.
6. N-(Benzyl)-1-(4-chlorophenyl)-2-(2,4-dichlorophenyl)-N-methyl-1H-imidazole-4-carboxamide; MS: 470.
7. 1-[1-(4-Chlorophenyl)-2-(2,4-dichlorophenyl)-4-(1H-imidazolyl)carbonyl]hexahydro-1H-azepine; MS: 448.
8. 2-(4-Chlorophenyl)-1-(2,4-dichlorophenyl)-N-(piperidin-1-yl)-1H-imidazole-4-carboxamide (prepared from 2,4-dichloroaniline and 4-chlorobenzo-nitrile); MS: 449.
9. N-(t-Butoxy)-2-(4-chlorophenyl)-1-(2,4-dichlorophenyl)-1H-imidazole-4-carboxamide (prepared from 2,4-dichloroaniline and 4-chlorobenzonitrile); MS: 438.

EXAMPLE 10

Part A: Diisopropylamine (2.30 gram, 22.8 mmol) is added dropwise to anhydrous THF (100 mL) in a nitrogen atmosphere at 0° C. n-BuLi is added dropwise (7.34 mL, 2.5 M solution in hexane, 18.4 mmol). The resulting solution is cooled to −78° C. A solution of ethyl 2-(4-chlorophenyl)-1-(2,4-dichlorophenyl)-1H-imidazole-4-carboxylate (6.0 gram, 15.2 mmol) in anhydrous THF is added dropwise. The colour of the mixture changes from yellow to purple brown. The stirred mixture is warmed to −40° C. and cooled to −78° C. and allowed to stand for 30 minutes. Methyl iodide (6.44 gram, 45.4 mmol) is added dropwise and the resulting solution is stirred for 30 min at −78° C. and then allowed to attain room temperature. The resulting solution is quenched with an aqueous $NH_4Cl$ solution, diethyl ether is added and the organic layer is dried over $MgSO_4$, filtered and concentrated in vacuo to give an oil (6.4 gram). This oil is purified by column chromatography (toluene/EtOAc=10/2 (v/v), silicagel) to give pure ethyl 2-(4-chlorophenyl)-1-(2,4-dichlorophenyl)-5-methyl-1H-imidazole-4-carboxylate (5.3 gram, 85% yield) as a yellow oil.

Part B: Ethyl 2-(4-chlorophenyl)-1-(2,4-dichlorophenyl)-5-methyl-1H-imidazole-4-carboxylate (0.250 gram, 0.61 mmol) and LiOH (0.052 gram, 2.17 mmol) are dissolved in $H_2O$/THF (1:1 (v/v); 50 mL) and stirred at 50° C. for one hour. The mixture is concentrated to give crude 2-(4-chlorophenyl)-1-(2,4-dichlorophenyl)-5-methyl-1H-imidazole-4-carboxylic acid. To this mixture is added $SOCl_2$ (50 mL) and the resulting mixture is heated at reflux temperature for 1 hour. The mixture is concentrated to give 2-(4-chlorophenyl)-1-(2,4-dichlorophenyl)-5-methyl-1H-imidazole-4-carbonyl chloride.

Part C: 2-(4-Chlorophenyl)-1-(2,4-dichlorophenyl)-5-methyl-1H-imidazole-4-carbonyl chloride (1.5 gram, 3.75 mmol), 1-aminopiperidine (0.725 gram, 7.25 mmol) and triethylamine (0.549 gram, 5.44 mmol) are dissolved in dichloromethane and stirred for one hour at room temperature. The mixture is washed with a saturated aqueous $NaHCO_3$ solution, dried over $Na_2SO_4$ and concentrated in vacuo and further purified by column chromatography (heptane/ethyl acetate=1/1 (v/v), silicagel) to give 2-(4-chlorophenyl)-1-(2,4-dichlorophenyl)-5-methyl-N-(piperidin-1-yl)-1H-imidazole-4-carboxamide (0.220 gram, 13% yield) as a white foam. MS: 463.

Analogously were prepared:
11. N-(t-Butoxy)-2-(4-chlorophenyl)-1-(2,4-dichlorophenyl)-5-methyl-1H-imidazole-4-carboxamide: MS: 452.
12. 1-(4-Chlorophenyl)-2-(2,4-dichlorophenyl)-5-methyl-N-(piperidin-1-yl)-1H-imidazole-4-carboxamide: MS: 463; Melting point: 165-167° C.
13. N-(t-Butoxy)-2-(4-chlorophenyl)-1-(4-chlorophenyl)-5-methyl-1H-imidazole-4-carboxamide: MS: 452.
14. N-(t-Butoxy)-1-(4-chlorophenyl)-2-(2,4-dichlorophenyl)-5-ethyl-1H-imidazole-4-carboxamide: Amorphous. MS: 468.
15. 1-(4-Chlorophenyl)-2-(2,4-dichlorophenyl)-5-ethyl-N-(piperidin-1-yl)-1H-imidazole-4-carboxamide: MS: 477.
16. 1-(4-Bromophenyl)-N-(t-butoxy)-2-(2,4-dichlorophenyl)-5-methyl-1H-imidazole-4-carboxamide: Amorphous.
17. 1-(4-Bromophenyl)-2-(2,4-dichlorophenyl)-5-methyl-N-(piperidin-1-yl)-1H-imidazole-4-carboxamide: MP: >204° C. TLC (Silicagel, EtOAc) $R_f$=0.3.
18. 1-(4-Bromophenyl)-N-(t-butoxy)-2-(2,4-dichlorophenyl)-5-ethyl-1H-imidazole-4-carboxamide: Amorphous. TLC (Silicagel, $CH_2Cl_2$/acetone=9/1 (v/v)) $R_f$=0.45.
19. 1-(4-Bromophenyl)-2-(2,4-dichlorophenyl)-5-ethyl-N-(piperidin-1-yl)-1H-imidazole-4-carboxamide: MP: >140° C. TLC (Silicagel, EtOAc) $R_f$=0.4.
20. 1-(4-Bromophenyl)-N-cyclohexyl-2-(2,4-dichlorophenyl)-5-ethyl-1H-imidazole-4-carboxamide: Melting point >135-140° C.
21. 1-(4-Bromophenyl)-2-(2,4-dichlorophenyl)-5-ethyl-N-(n-pentyl)-1H-imidazole-4-carboxamide: Syrup. TLC (Silicagel, $CH_2Cl_2$/acetone=19/1 (v/v)) $R_f$=0.4.

EXAMPLE 22

Part A: To a stirred solution of ethyl 1-(4-bromophenyl)-2-(2,4-dichlorophenyl)-1H-imidazole-4-carboxylate (6.10 gram, 0.0139 mol) in THF (70 mL) is added LiOH (0.67 gram, 0.0278 mol) and water (70 mL). The resulting mixture is stirred for 16 hours at 50° C. to give a clear solution. After cooling to room temperature, HCl (1N solution, 28 mL) is added to give an oily precipitate which completely solidifies on continued stirring and addition of water (70 mL). The precipitate is collected by filtration, washed with water and dried in vacuo to give 1-(4-bromophenyl)-2-(2,4-dichlorophenyl)-1H-imidazole-4-carboxylic acid (4.92 gram, 86% yield). Melting point: 138-142° C.

Part B: To a stirred suspension of 1-(4-bromophenyl)-2-(2,4-dichlorophenyl)-1H-imidazole-4-carboxylic acid (1.23 gram, 2.99 mmol) in dry acetonitrile (40 mL) is successively added diisopropylethylamine (DIPEA) (1.15 mL, 6.6 mmol), O-benzotriazol-1-yl-N,N,N',N'-tetramethyluronium hexafluorophos-phate (HBTU) (1.36 gram, 3.6 mmol) and 1-aminopiperidine (0.39 mL, 3.6 mmol). After stirring for 16 hours, the resulting mixture is concentrated in vacuo. The residue is dissolved in ethylacetate and an aqueous $NaHCO_3$ solution is added. The ethylacetate layer is collected, washed with water and brine, dried over $Na_2SO_4$, filtered and concentrated in vacuo to give a crude solid. This solid is further purified by recrystallisation from acetonitrile to give 1-(4-bromophenyl)-2-(2,4-dichlorophenyl)-N-(piperidin-1-yl)-1H-imidazole-4-carboxamide (830 mg, 56% yield). Melting point: 219-221° C.

Analogously were prepared:
23. N-(t-Butoxy)-1-(4-bromophenyl)-2-(2,4-dichlorophenyl)-1H-imidazole-4-carboxamide. Amorphous. TLC (Silicagel, $Et_2O$) $R_f$=0.3.
24. 1-(4-Bromophenyl)-2-(2,4-dichlorophenyl)-N-(pyrrolidin-1-yl)-1H-imidazole-4-carboxamide. Melting point: 238-240° C.
25. N-(Azepan-1-yl)-1-(4-bromophenyl)-2-(2,4-dichlorophenyl)-1H-imidazole-4-carboxamide. Melting point: 201-204° C.
26. 1-(4-Chlorophenyl)-2-(2,4-dichlorophenyl)-N-(hexahydrocyclopenta[c]pyrrol 2(1H)-yl)-1H-imidazole-4-carboxamide. MS: 475.

27. 1-(4-Chlorophenyl)-2-(2,4-dichlorophenyl)-N-(4-fluorobenzyl)-1H-imidazole-4-carboxamide. MS: 474.
28. 1-(4-Chlorophenyl)-2-(2-methoxy-4-chlorophenyl)-N-(piperidin-1-yl)-1H-imidazole-4-carboxamide. Melting point: 220° C.
29. 1-(4-Chlorophenyl)-N-cyclohexyl-2-(2-methoxy-4-chlorophenyl)-1H-imidazole-4-carboxamide. Melting point: 177-179° C.
30. 1-(4-Chlorophenyl)-2-(2-fluoro-4-chlorophenyl)-N-(piperidin-1-yl)-1H-imidazole-4-carboxamide. Melting point: 217-218° C.
31. 2-(2,4-Dichlorophenyl)-1-(4-fluorophenyl)-N-(piperidin-1-yl)-1H-imidazole-4-carboxamide. Melting point: 175-176° C.
32. N-Cyclohexyl-2-(2,4-dichlorophenyl)-1-(4-fluorophenyl)-1H-imidazole-4-carboxamide. Melting point: 184-185° C.
33. N-Cyclohexyl-2-(2-fluoro-4-chlorophenyl)-1-(4-chlorophenyl)-1H-imidazole-4-carboxamide. Melting point: 157-159° C.
34. 1-(4-Chlorophenyl)-2-(2-methoxy-4-chlorophenyl)-N-(n-pentyl)-1H-imidazole-4-carboxamide. Melting point: 115° C.
35. 2-(2,4-Dichlorophenyl)-1-(4-methoxyphenyl)-N-(piperidin-1-yl)-1H-imidazole-4-carboxamide. Melting point: 178-179° C.
36. N-Cyclohexyl-2-(2,4-dichlorophenyl)-1-(4-methoxyphenyl)-1H-imidazole-4-carboxamide. Melting point: 175-176° C.
37. 1-(4-Chlorophenyl)-2-(2,4-dichlorophenyl)-N,N-diethyl-1H-imidazole-4-carboxamide. Melting point: 177-179° C.
38. 1-(4-Chlorophenyl)-N-cyclohexyl-2-(2-trifluoromethyl-4-chlorophenyl)-1H-imidazole-4-carboxamide. Melting point: 172° C.
39. 1-(4-Chlorophenyl)-N-(piperidin-1-yl)-2-(2-trifluoromethyl-4-chlorophenyl)-1H-imidazole-4-carboxamide. Melting point: 219° C.
40. N-(1-Adamantyl)-1-(4-chlorophenyl)-2-(2-trifluoromethyl-4-chlorophenyl)-1H-imidazole-4-carboxamide. Melting point: 288° C.
41. 1-(4-Chlorophenyl)-N-(2,2,2-trifluoroethyl)-2-(2-trifluoromethyl-4-chlorophenyl)-1H-imidazole-4-carboxamide. Melting point: 149° C.
42. 2-(2,4-Dichlorophenyl)-1-(pyridin-3-yl)-N-(piperidin-1-yl)-1H-imidazole-4-carboxamide. Melting point: 165-170° C.
43. N-Cyclohexyl-2-(2,4-dichlorophenyl)-1-(pyridin-3-yl)-1H-imidazole-4-carboxamide. Melting point: 195° C.
44. 2-(2,4-Dichlorophenyl)-1-(pyridin-3-yl)-N-(n-pentyl)-1H-imidazole-4-carboxamide. Melting point: 117° C.

EXAMPLE 45

Part A: 2,4-Dichlorobenzoyl chloride (40.0 g, 0.19 mol) is dissolved in tetrahydrofuran (1 L). To the resulting stirred solution is successively added diisopropylethylamine (DIPEA) (73.4 mL, 2.2 molar equivalent) and 4-(trifluoromethyl)phenylamine (30.7 g, 0.19 mol). After one hour the mixture is concentrated in vacuo to give an oil. This oil is crystallised from ethanol to give pure 2,4-dichloro-N-(4-(trifluoromethyl)phenyl)benzamide (53.2 g, 83% yield). $^1$H-NMR (200 MHz, DMSO-$d_6$): δ 10.90 (br s, 1H), 7.91 (br d, J=8 Hz, 2H), 7.63-7.77 (m, 4H), 7.57 (dt, J=8 Hz, J=2 Hz, 1H).

Part B: 2,4-Dichloro-N-(4-(trifluoromethyl)phenyl)benzamide (19.0 g, 0.057 mol) is dissolved in benzene (150 mL) and PCl$_5$ (13.0 g, 1.1 molar equivalent) is added. The resulting mixture is heated at reflux temperature for two hours, allowed to attain room temperature and concentrated in vacuo to give a residue. The residue is dissolved in anhydrous THF, cooled to 0° C. and transferred into an autoclave. Excess NH$_3$ is quickly added from a lecture bottle and the mixture is stirred at room temperature for 50 hours. A mixture of ethylacetate and aqueous NaHCO$_3$ is added. The ethylacetate layer is collected, dried over Na$_2$SO$_4$, filtered and concentrated in vacuo. The resulting oil is purified by column chromatography (diethyl ether/petroleum ether=1/1 (v/v), silicagel) to give pure 2,4-dichloro-N-(4-(trifluoromethyl)phenyl)benzene-carboxamidine (16.9 g, 89% yield). Melting point: 108-109° C.

Part C: 2,4-Dichloro-N-(4-(trifluoromethyl)phenyl)benzenecarboxamidine (15.0 g, 0.0450 mol) is dissolved in 2-propanol and ethyl 3-bromo-2-oxobutanoate (20.8 g, 2 molar equivalent) and NaHCO$_3$ are successively added. The resulting mixture is heated at reflux temperature for 40 hours and allowed to attain room temperature. The 2-propanol is removed in vacuo, ethyl acetate is added to the residue and the resulting organic layer is washed with NaHCO$_3$ (5% aqueous solution). The ethylacetate layer is collected, dried over Na$_2$SO$_4$, filtered and concentrated in vacuo. The resulting oil is purified by column chromatography (diethyl ether/petroleum ether=1/3 (v/v), silicagel) and further purified by crystallisation from cyclohexane to give ethyl 2-(2,4-dichlorophenyl)-5-methyl-1-(4-(trifluoromethyl)phenyl)-1H-imidazole-4-carboxylate (10.45 g, 52% yield) as a yellow solid. Melting point: 160-162° C.

Part D: The formed ethyl 2-(2,4-dichlorophenyl)-5-methyl-1-(4-(trifluoromethyl)phenyl)-1H-imidazole-4-carboxylate is converted to 2-(2,4-dichlorophenyl)-5-methyl-1-(4-(trifluoromethyl)phenyl)-1H-imidazole-4-carboxylic acid (melting point: 224-226° C.), which carboxylic acid is converted to 2-(2,4-dichlorophenyl)-5-methyl-N-(piperidin-1-yl)-1-(4-(trifluoromethyl)phenyl)-1H-imidazole-4-carboxamide (melting point: 173-174° C.) according to the procedure described in example 22 above. Analogously were prepared
46. 2-(2,4-dichlorophenyl)-N-(piperidin-1-yl)-1-(4-(trifluoromethyl)phenyl)-1H-imidazole-4-carboxamide. Melting point: >200° C. (decomposition).
47. N-Cyclohexyl-2-(2,4-dichlorophenyl)-5-methyl-1-(4-(trifluoromethyl)phenyl)-1H-imidazole-4-carboxamide. Melting point: 178-179° C.
48. N-Cyclohexyl-2-(2,4-dichlorophenyl)-1-(4-(trifluoromethyl)phenyl)-1H-imidazole-4-carboxamide. Melting point: 199-200° C.

EXAMPLE 49

Part A: N-(4-methoxyphenyl)-2,4-dichlorobenzenecarboxamidine (15.0 gram, 50.8 mmol) is dissolved in 2-propanol and ethyl 3-bromo-2-oxobutanoate (23.5 g, 2 molar equivalents) and NaHCO$_3$ (8.5 gram, 2 molar equivalents) are successively added. The resulting mixture is heated at reflux temperature for 40 hours and allowed to attain room temperature. The 2-propanol is removed in vacuo, ethyl acetate is added to the residue and the resulting organic layer is washed with NaHCO$_3$ (5% aqueous solution). The ethylacetate layer is collected, dried over Na$_2$SO$_4$, filtered and concentrated in vacuo. The resulting oil is purified by column chromatography (diethyl ether/petroleum ether=1/3 (v/v), silicagel) to give ethyl 2-(2,4-dichlorophenyl)-5-methyl-1-(4-methoxyphenyl)-1H-imidazole-4-carboxylate (8.61 g, 42% yield) as a solid. $^1$H-NMR (200 MHz, CDCl$_3$): δ 7.33 (d, J=8 Hz, 1H), 7.27 (d, J=2 Hz, 1H), 7.18 (dd, J=8 Hz, J=2 Hz, 1H), 7.03 (dt, J=8 Hz, J=2 Hz, 2H), 6.85 (dt, J=8 Hz, J=2 Hz, 2H), 4.42 (q, J=7 Hz, 2H), 3.80 (s, 3H), 2.43 (s, 3H), 1.43 (t, J=7 Hz, 3H).

Part B: To a stirred solution of ethyl 2-(2,4-dichlorophenyl)-5-methyl-1-(4-methoxyphenyl)-1H-imidazole-4-carboxylate (8.00 gram, 0.0198 mol) in THF (80 mL) is added LiOH (0.59 gram, 2 molar equivalents) and water (80 mL). The resulting mixture is stirred for 16 hours at 80° C. After cooling to room temperature, HCl (2N solution, 12.3 mL) is added to give an oily precipitate. After addition of water and extraction with ethylacetate, the ethylacetate layer is collected, dried over $Na_2SO_4$, filtered and concentrated in vacuo. The residue is crystallised from diisopropyl ether and dried to give 2-(2,4-dichlorophenyl)-5-methyl-1-(4-methoxyphenyl)-1H-imidazole-4-carboxylic acid (4.04 gram, 87% yield) as a pale grey solid. Melting point: 189-191° C.

Part C: To 2-(2,4-dichlorophenyl)-5-methyl-1-(4-methoxyphenyl)-1H-imidazole-4-carboxylic acid (1.00 gram, 2.65 mmol) in dry acetonitrile (25 mL) is successively added diisopropylethylamine (DIPEA) (1.02 mL, 2.2 molar equivalents), O-benzotriazol-1-yl-N,N,N',N'-tetramethyluronium hexafluoro-phosphate (HBTU) (1.21 gram, 1.2 molar equivalents) and the resulting solution is stirred for 15 minutes. Cyclohexylamine (0.36 mL, 1.2 molar equivalents) is added. After stirring for 50 hours, the resulting mixture is concentrated in vacuo. The residue is dissolved in dichloromethane and an aqueous $NaHCO_3$ solution is added. The dichloromethane layer is collected, dried over $Na_2SO_4$, filtered and concentrated in vacuo. The residue is further purified by column chromatography (gradient: dichloromethane=>dichloromethane/methanol=99/1 (v/v), silicagel) to give N-(1-cyclohexyl)-2-(2,4-dichlorophenyl)-5-methyl-1-(4-methoxyphenyl)-1H-imidazole-4-carboxamide (1.03 gram, 85% yield). Melting point: 160-161° C.

Analogously were prepared:

50. 1-(4-Chlorophenyl)-2-(2,4-dichlorophenyl)-N,N,5-trimethyl-1H-imidazole-4-carboxamide. Melting point: 101-104° C.
51. 1-(4-Chloropyridin-2-yl)-2-(2,4-dichlorophenyl)-5-methyl-N-(piperidin-1-yl)-1H-imidazole-4-carboxamide. MS: 464 (MH$^+$).
52. 1-(4-Chloropyridin-2-yl)-2-(2,4-dichlorophenyl)-5-methyl-N-(4-morpholinyl)-1H-imidazole-4-carboxamide. MS: 466 (MH$^+$).
53. N-(1-Azepanyl)-1-(4-Chloropyridin-2-yl)-2-(2,4-dichlorophenyl)-5-methyl-1H-imidazole-4-carboxamide. MS: 478 (MH$^+$).
54. 1-(4-Chloropyridin-2-yl)-N-cyclohexyl-2-(2,4-dichlorophenyl)-5-methyl-1H-imidazole-4-carboxamide. MS: 463.
55. 1-(4-Chloropyridin-2-yl)-2-(2,4-dichlorophenyl)-5-methyl-N-(n-pentyl)-1H-imidazole-4-carboxamide. MS: 451.
56. 1-(4-Chloropyridin-2-yl)-2-(2,4-dichlorophenyl)-N-(4-fluorobenzyl)-5-methyl-1H-imidazole-4-carboxamide. MS: 489. Melting point: 123-126° C.
57. 1-(4-Chlorophenyl)-N-cyclohexyl-5-methyl-2-(2-trifluoromethyl-4-chlorophenyl)-1H-imidazole-4-carboxamide. Melting point: 212° C.
58. 1-(4-Chlorophenyl)-5-methyl-N-(piperidin-1-yl)-2-(2-trifluoromethyl-4-chlorophenyl)-1H-imidazole-4-carboxamide. Melting point: 165° C.
59. 1-(4-Chlorophenyl)-2-(2-methoxy-4-chlorophenyl)-5-methyl-N-(n-pentyl)-1H-imidazole-4-carboxamide. Melting point: 131° C.
60. 1-(4-Chlorophenyl)-2-(2-methoxy-4-chlorophenyl)-5-methyl-N-(piperidin-1-yl)-1H-imidazole-4-carboxamide. Melting point: >256° C.
61. N-Cyclohexyl-1-(4-chlorophenyl)-2-(2-methoxy-4-chlorophenyl)-5-methyl-1H-imidazole-4-carboxamide. Melting point: 201° C.
62. 2-(2,4-Dichlorophenyl)-1-(4-fluorophenyl)-5-methyl-N-(piperidin-1-yl)-1H-imidazole-4-carboxamide. Melting point: 223-224° C.
63. 2-(2,4-Dichlorophenyl)-5-methyl-1-(4-methoxyphenyl)-N-(piperidin-1-yl)-1H-imidazole-4-carboxamide. Melting point: >90° C. (decomposition).
64. N-Cyclohexyl-1-(4-fluorophenyl)-2-(2,4-dichlorophenyl)-5-methyl-1H-imidazole-4-carboxamide. Melting point: 229-230° C.
65. 1-(4-Chlorophenyl)-5-methyl-N-(n-pentyl)-2-(2-trifluoromethyl-4-chlorophenyl)-1H-imidazole-4-carboxamide. Amorphous.
66. 1-(4-Chlorophenyl)-2-(2-fluoro-4-chlorophenyl)-5-methyl-N-(piperidin-1-yl)-1H-imidazole-4-carboxamide. Melting point: 195° C.
67. 1-(4-Chlorophenyl)-2-(2-fluoro-4-chlorophenyl)-5-methyl-N-(n-pentyl)-1H-imidazole-4-carboxamide. Melting point: 115° C.
68. 1-(4-Chlorophenyl)-N-(cyclohexyl)-2-(2-fluoro-4-chlorophenyl)-5-methyl-1H-imidazole-4-carboxamide. Melting point: 188° C.
69. 1-(4-Chlorophenyl)-N-(cyclohexyl)-2-(1,5-dimethyl-1H-pyrrol-2-yl)-5-methyl-1H-imidazole-4-carboxamide. Melting point: 188-189° C.
70. 1-(4-Chlorophenyl)-2-(1,5-dimethyl-1H-pyrrol-2-yl)-5-methyl-N-(piperidin-1-yl)-1H-imidazole-4-carboxamide. Melting point: 208-210° C.
71. 2-(2-Chlorophenyl)-1-(3-fluorophenyl)-5-methyl-N-(piperidin-1-yl)-1H-imidazole-4-carboxamide. Melting point: 236-238° C.
72. 2-(2-Chlorophenyl)-1-(3-fluorophenyl)-5-methyl-N-(n-pentyl)-1H-imidazole-4-carboxamide. Melting point: 97-102° C.
73. 2-(2-Chlorophenyl)-N-cyclohexyl-1-(3-fluorophenyl)-5-methyl-1H-imidazole-4-carboxamide. Melting point: 180-182.5° C.
74. 2-(2-Chlorophenyl)-1-(3-fluorophenyl)-N-(2-(4-fluorophenyl)ethyl)-5-methyl-1H-imidazole-4-carboxamide. Melting point: 123.5-126° C.
75. 1-(4-Chloropyridin-2-yl)-2-(2,4-dichlorophenyl)-5-ethyl-N-(piperidin-1-yl)-1H-imidazole-4-carboxamide. Melting point: 146° C.
76. 1-(4-Chloropyridin-2-yl)-2-(2,4-dichlorophenyl)-5-ethyl-N-(4-morpholinyl)-1H-imidazole-4-carboxamide. Melting point: 223° C.
77. N-(1-Azepanyl)-1-(4-Chloropyridin-2-yl)-2-(2,4-dichlorophenyl)-5-ethyl-1H-imidazole-4-carboxamide. Melting point: 177° C.
78. 1-(4-Chloropyridin-2-yl)-N-cyclohexyl-2-(2,4-dichlorophenyl)-5-ethyl-1H-imidazole-4-carboxamide. Melting point: 149° C.
79. 1-(4-Chloropyridin-2-yl)-2-(2,4-dichlorophenyl)-5-ethyl-N-(n-pentyl)-1H-imidazole-4-carboxamide. Melting point: Oil.
80. 1-(4-Chloropyridin-2-yl)-2-(2,4-dichlorophenyl)-5-ethyl-N-(4-fluorophenylmethyl)-1H-imidazole-4-carboxamide. MP: amorphous.
81. 1-(4-Chlorophenyl)-2-(2,4-dichlorophenyl)-N-(hexahydrocyclopenta-[c]pyrrol-2(1H)-yl)-5-methyl-1H-imidazole-4-carboxamide. MP: 143-146° C.
82. 1-(4-Chlorophenyl)-2-(2,4-dichlorophenyl)-5-methyl-N-phenyl-1H-imidazole-4-carboxamide. Melting point: 91-95° C.

83. 1-(4-Chlorophenyl)-2-(2,4-dichlorophenyl)-5-methyl-N-(tetrahydro-2H-pyran-2-yloxy)-1H-imidazole-4-carboxamide. Melting point: 128-133° C.
84. N-(Exo-bicyclo[2.2.1]hept-2-yl)-1-(4-chlorophenyl)-2-(2,4-dichlorophenyl)-5-methyl-1H-imidazole-4-carboxamide. Melting point: 194-195° C.
85. 1-(4-Chlorophenyl)-2-(2,4-dichlorophenyl)-N-(2-fluoroethyl)-5-methyl-1H-imidazole-4-carboxamide. Melting point: 128-133° C.
86. 1-(4-Chlorophenyl)-2-(2,4-dichlorophenyl)-N-(trans-4-hydroxycyclohexyl)-5-methyl-1H-imidazole-4-carboxamide. Melting point: 160° C. (dec.).
87. 1-{[1-(4-Chlorophenyl)-2-(2,4-dichlorophenyl)-5-methyl-1H-imidazol-4-yl]carbonyl}-4-hydroxypiperidine. Melting point: Amorphous.
88. 1-{[1-(4-Chlorophenyl)-2-(2,4-dichlorophenyl)-5-methyl-1H-imidazol-4-yl]carbonyl}-1,2,3,4-tetrahydroisoquinoline. Melting point: 143-146° C.
89. N-(Endo-bicyclo[2.2.1]hept-2-yl)-1-(4-chlorophenyl)-2-(2,4-dichlorophenyl)-5-methyl-1H-imidazole-4-carboxamide. Melting point: 194-195° C.
90. 1-(4-Chlorophenyl)-2-(2,4-dichlorophenyl)-N-(4-fluorobenzyl)-5-methyl-1H-imidazole-4-carboxamide. Melting point: 165-166° C.
91. 1-(4-Chlorophenyl)-2-(2,4-dichlorophenyl)-5-methyl-N-(n-pentyl)-1H-imidazole-4-carboxamide. Oil.
92. N-(Azepan-1-yl)-1-(4-chlorophenyl)-2-(2,4-dichlorophenyl)-5-methyl-1H-imidazole-4-carboxamide. Melting point: 147-149° C.
93. 1-(4-Chlorophenyl)-2-(2,4-dichlorophenyl)-5-methyl-N-(pyrrolidin-1-yl)-1H-imidazole-4-carboxamide. Melting point: 205-206° C.
94. 1-(4-Chlorophenyl)-2-(2,4-dichlorophenyl)-5-methyl-N-(morpholin-4-yl)-1H-imidazole-4-carboxamide. Melting point: 225° C. (dec.).
95. 2-(2,5-Dichlorophenyl)-5-methyl-1-phenyl-N-(piperidin-1-yl)-1H-imidazole-4-carboxamide. Melting point: 227° C.
96. N-Cyclohexyl-2-(2,5-dichlorophenyl)-5-methyl-1-phenyl-1H-imidazole-4-carboxamide. Melting point: 236° C.
97. N-Cyclohexyl-2-(2,4-dichlorophenyl)-1-(2,5-difluorophenyl)-5-ethyl-1H-imidazole-4-carboxamide. Melting point: 144-146° C.
98. N-Cyclohexyl-2-(2,4-dichlorophenyl)-1-(2,5-difluorophenyl)-5-methyl-1H-imidazole-4-carboxamide. Melting point: 206-208° C.
99. N-Cyclohexyl-2-(1,5-dimethyl-1H-pyrrol-2-yl)-5-ethyl-1-phenyl-1H-imidazole-4-carboxamide. Melting point: 195-196° C.
100. N-Cyclohexyl-2-(2,5-dichlorophenyl)-5-ethyl-1-phenyl-1H-imidazole-4-carboxamide. Melting point: 198-199° C.
101. 2-(2,5-Dichlorophenyl)-5-ethyl-1-phenyl-N-(piperidin-1-yl)-1H-imidazole-4-carboxamide. Melting point: 207-208° C.
102. 1-(4-Chlorophenyl)-5-methyl-2-(3-methylpyridin-2-yl)-N-(piperidin-1-yl)-1H-imidazole-4-carboxamide. Melting point: 211-213° C.
103. 1-(4-Chlorophenyl)-N-cyclohexyl-5-methyl-2-(3-methylpyridin-2-yl)-1H-imidazole-4-carboxamide. Melting point: 188-190° C.
104. 1-(4-Chlorophenyl)-2-(2,4-dichlorophenyl)-5-methyl-N-(3-(trifluoromethyl)phenyl)-1H-imidazole-4-carboxamide. Melting point: 177° C.
105. 1-(4-Chlorophenyl)-2-(2,4-dichlorophenyl)-5-methyl-N-(3-(trifluoromethyl)benzyl)-1H-imidazole-4-carboxamide. Melting point: 138-140° C.
106. 1-(4-Chlorophenyl)-2-(2,4-dichlorophenyl)-5-methyl-N-(4-(trifluoromethyl)benzyl)-1H-imidazole-4-carboxamide. Melting point: 232° C.
107. 1-(4-Chlorophenyl)-N-cyclopentyl-2-(2,4-dichlorophenyl)-5-methyl-1H-imidazole-4-carboxamide. Melting point: 172° C.
108. 1-(4-Chlorophenyl)-N-cycloheptyl-2-(2,4-dichlorophenyl)-5-methyl-1H-imidazole-4-carboxamide. Melting point: 154-156° C.

EXAMPLE 109

Part A: Ethyl 1-(4-bromophenyl)-2-(2,4-dichlorophenyl)-1H-imidazole-4-carboxylate is converted to ethyl 1-(4-bromophenyl)-5-chloro-2-(2,4-dichlorophenyl)-1H-imidazole-4-carboxylate analogously to a published procedure (N. Kudo et al., *Chem. Pharm. Bull.* 1999, 47, 857-868) using excess of $SO_2Cl_2$ in dichloroethane at reflux temperature for 50 hours.

Part B: Ethyl 1-(4-bromophenyl)-5-chloro-2-(2,4-dichlorophenyl)-1H-imidazole-4-carboxylate is converted to 1-(4-bromophenyl)-5-chloro-2-(2,4-dichloro-phenyl)-N-(piperidin-1-yl)-1H-imidazole-4-carboxamide (melting point: >150° C.; $R_f$ (Silicagel, EtOAc) ~0.35) analogously to the procedure described in example 22 above. $^1$H-NMR (400 MHz, $CDCl_3$): δ 7.85 (br s, 1H), 7.52 (dt, J=8 Hz, J=2 Hz, 2H), 7.26-7.36 (m, 3H), 7.01 (dt, J=8 Hz, J=2 Hz, 2H), 2.85-2.92 (m, 4H), 1.72-1.80 (m, 4H), 1.40-1.44 (m, 2H).

EXAMPLE 110

Part A: To a stirred solution of 1-(4-chlorophenyl)-2-(2,4-dichlorophenyl)-1H-imidazole-4-carboxylic acid (18.38 gram, 50 mmol) in toluene (200 mL) in a nitrogen atmosphere is added N,N-dimethylformamide di-tert-butyl acetal (50 mL) and the resulting mixture is heated at 80° C. for 4 hours. After cooling to room temperature the reaction mixture is concentrated and diethyl ether is added. The resulting solution is twice washed with water, dried over $MgSO_4$, filtered and concentrated in vacuo. The residue is crystallised from diisopropyl ether to give pure tert-butyl 1-(4-chlorophenyl)-2-(2,4-dichlorophenyl)-1H-imidazole-4-carboxylate (10.35 gram, 49% yield). Melting point: 179-181° C.

Part B:

Lithium diisopropyl amide (LDA) (5.25 mL of a 2 M solution in THF, 0.0105 mol) is added dropwise to a cooled solution (−70° C.) of tert-butyl 1-(4-chlorophenyl)-2-(2,4-dichlorophenyl)-1H-imidazole-4-carboxylate (4.24 gram, 0.010 mol) in anhydrous THF (80 mL) in a nitrogen atmosphere and the resulting mixture is stirred for one hour. A solution of p-toluenesulfonyl cyanide (1.88 gram, 0.011 mol) in anhydrous THF (20 mL) is added dropwise and the resulting red solution is stirred for one hour at −70° C. and then allowed to attain room temperature. Diethyl ether is added and the resulting solution is quenched with water and filtered over hyflo. The organic layer is collected and washed with water, dried over $MgSO_4$, filtered and concentrated in vacuo to give an oil. This oil is purified by column chromatography (dichloromethane, silicagel) to give 3.4 gram of tert-butyl 1-(4-chlorophenyl)-5-cyano-2-(2,4-dichlorophenyl)-1H-imidazole-4-carboxylate. Recrystallisation from diisopropyl ether gave crystalline tert-butyl 1-(4-chlorophenyl)-5-cyano-2-(2,4-dichlorophenyl)-1H-imidazole-4-carboxylate (2.57 gram, 57% yield). Melting point: 210-212° C.

Analogously was prepared:

Tert-butyl 1-(4-chlorophenyl)-2-(2,4-dichlorophenyl)-5-methyl-1H-imidazole-4-carboxylate. $^1$H-NMR (400 MHz, $CDCl_3$): δ 7.38 (d, J=8 Hz, 1H), 7.34 (dt, J=8 Hz, J=2 Hz, 2H), 7.27 (d, J=2 Hz, 1H), 7.22 (dd, J=8 Hz, J=2 Hz, 1H), 7.03 (dt, J=8 Hz, J=2 Hz, 2H), 2.40 (s, 3H), 1.63 (s, 9H).

Part C:

To a solution of tert-butyl 1-(4-chlorophenyl)-2-(2,4-dichlorophenyl)-5-cyano-1H-imidazole-4-carboxylate (2.57 gram, 5.73 mmol) in dichloromethane (40 mL) is added trifluoroacetic acid and the resulting solution is stirred at room temperature for 20 hours and concentrated in vacuo. The residue is crystallised from diisopropyl ether to give pure 1-(4-chlorophenyl)-5-cyano-2-(2,4-dichlorophenyl)-1H-imidazole-4-carboxylic acid (1.95 gram, 87% yield). Melting point: 200-202° C. (dec.).

Part D:

1-(4-Chlorophenyl)-5-cyano-2-(2,4-dichlorophenyl)-1H-imidazole-4-carboxylic acid is converted to 1-(4-chlorophenyl)-5-cyano-2-(2,4-dichlorophenyl)-N-(piperidin-1-yl)-1H-imidazole-4-carboxamide in 60% yield, analogously to the procedure described in example 22, part B herein above. Melting point: 231-233.5° C.

Analogously were prepared:

111. 1-(4-Chlorophenyl)-2-(2,4-dichlorophenyl)-5-iodo-N-(piperidin-1-yl)-1H-imidazole-4-carboxamide. Melting point: 196-201° C.
112. 1-(4-Chlorophenyl)-N-cyclohexyl-2-(2,4-dichlorophenyl)-5-iodo-1H-imidazole-4-carboxamide. Melting point: 226-230° C.
113. 1-(4-Chlorophenyl)-5-cyano-N-cyclohexyl-2-(2,4-dichlorophenyl)-1H-imidazole-4-carboxamide. Melting point: 157-158° C.

The invention claimed is:

1. A compound of formula (I)

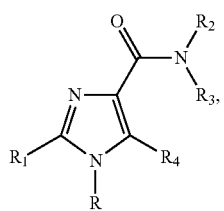

(I)

or a stereoisomer or salt thereof, wherein

R represents phenyl, thienyl, 2-pyridinyl, 3-pyridinyl, 4-pyridinyl, pyrimidinyl, pyrazinyl, pyradazinyl or triazinyl, which groups may be substituted with 1, 2, 3 or 4 substituents Y, which can be the same or different, and each is chosen from the group $C_{1-3}$-alkyl or alkoxy, hydroxyl, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkoxycarbonyl, carboxyl, cyano, carbamoyl and acetyl, or R represents naphthyl, with the proviso that when R is 4-pyridinyl or pyrimidinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, wherein the $C_{1-4}$ alkyl group may be substituted with 1-3 fluoro atoms or with a bromo, chloro, iodo, cyano or hydroxy group, $R_1$ represents phenyl or pyridinyl groups, which groups may be substituted with 1-4 substituents Y, which can be the same or different, wherein Y has the above mentioned meaning, or $R_1$ represents pyrimidinyl, pyrazinyl, pyridazinyl or triazinyl, which groups may be substituted with 1-2 substituents Y, which can be the same or different, or $R_1$ represents naphtyl, $R_2$ represents H, branched or unbranched $C_{1-8}$ alkyl, $C_{3-8}$ cycloalkyl, $C_{3-8}$ alkenyl, or $C_{5-8}$ cycloalkenyl, which groups may contain a sulfur, oxygen or nitrogen atom, $R_3$ represents branched or unbranched $C_{2-8}$ alkyl, $C_{1-8}$ alkoxy, $C_{5-8}$ cycloalkyloxy, $C_{3-8}$ cycloalkyl, $C_{5-10}$ bicycloalkyl, $C_{6-10}$ tricycloalkyl, $C_{3-8}$ alkenyl, or $C_{5-8}$ cycloalkenyl, which groups may optionally contain one or more heteroatoms chosen from the group (O, N, S) and which groups may be substituted with a hydroxyl group or 1-2 $C_{1-3}$ alkyl groups or 1-3 fluoro atoms, or $R_3$ represents a benzyl or phenethyl group, which aromatic rings may be substituted with 1-5 substituents Z, which can be the same or different, and chosen from the group $C_{1-3}$-alkyl or alkoxy, hydroxyl, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkylsulfonyl, dimethyl-sulfamido, $C_{1-3}$ alkoxycarbonyl, carboxyl, trifluoromethylsulfonyl, cyano, carbamoyl, sulfamoyl and acetyl, or $R_3$ represents a phenyl or pyridinyl group, which groups are substituted with 1-4 substituents Z, wherein Z has the meaning as indicated above, with the proviso that when the phenyl or pyridinyl groups are unsubstituted, $R_4$ represents a halogen atom or a cyano, carbamoyl, formyl, acetyl, trifluoroacetyl, fluoroacetyl, propionyl, sulfamoyl, methanesulfonyl, methylsulfanyl or $C_{1-4}$ alkyl group, which $C_{1-4}$ alkyl group may be substituted with 1-3 fluoro atoms or with a bromo, chloro, iodo, cyano or hydroxyl group, or $R_3$ represents a group $NR_5R_6$, with the proviso that $R_2$ represents a hydrogen atom or a methyl group, wherein $R_5$ and $R_6$ are the same or different and represent branched or unbranched $C_{1-4}$ alkyl, or $R_5$ and $R_6$, together with the nitrogen atom to which they are bonded, form a saturated or unsaturated, monocyclic or bicyclic heterocyclic group having 4 to 10 ring atoms which heterocyclic group contains one or two heteroatoms chosen from the group (N, O, S), which heteroatoms can be the same or different, which heterocyclic group may be substituted with a $C_{1-3}$ alkyl group or a hydroxyl group, or $R_2$ and $R_3$, together with the nitrogen atom to which they are bonded, form a saturated or unsaturated heterocyclic group having 4 to 10 ring atoms which heterocyclic group contains one or two heteroatoms chosen from the group (N, O, S), which heteroatoms can be the same or different, and which heterocyclic group may be substituted with a $C_{1-3}$ alkyl group or a hydroxyl group, $R_4$ represents a hydrogen or halogen atom or a cyano, carbamoyl, formyl, acetyl, trifluoracetyl, fluoroacetyl, propionyl, sulfamoyl, methanesulfonyl, methylsulfanyl or branched or unbranched $C_{1-4}$ alkyl group, which $C_{1-4}$ alkyl group may be substituted with 1-3 fluoro atoms or with a bromo, chloro, iodo, cyano or a hydroxyl group, with the proviso that when R, $R_1$, and $R_3$ are phenyl, and $R_2$ is hydrogen, $R_4$ is not a methyl group;

with the proviso that when R is phenyl substituted with chloro, $R_1$ and $R_3$ are phenyl, and $R_2$ is hydrogen, $R_4$ is not a methyl group; and with the proviso that when R is phenyl substituted with methoxy, $R_1$ and $R_3$ are phenyl, and $R_2$ is hydrogen, $R_4$ is not a methyl group;

with the proviso that when R is phenyl substituted with chloro, $R_1$ is phenyl substituted with methoxy, $R_2$ is hydrogen, and $R_3$ is phenyl, $R_4$ is not a methyl group.

2. A pharmaceutical composition containing a pharmacologically active amount of at least one compound as claimed in 1 as an active component.

3. A method of preparing a pharmaceutical composition, comprising a pharmacologically active amount of at least one compound as claimed in claim 1 and at least one carrier, at least one auxiliary substance, or a combination thereof.

4. A process for the preparation of a compound of formula (I),

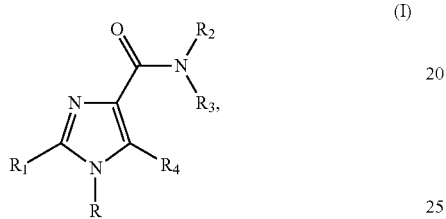

or a stereoisomer or salt thereof, wherein:

R represents phenyl, thienyl, 2-pyridinyl, 3-pyridinyl, 4-pyridinyl, pyrimidinyl, pyrazinyl, pyradazinyl or triazinyl, which groups may be substituted with 1, 2, 3 or 4 substituents Y, which can be the same or different, and each is chosen from the group $C_{1-3}$-alkyl or alkoxy, hydroxyl, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkoxycarbonyl, carboxyl, cyano, carbamoyl and acetyl, or R represents naphtyl, with the proviso that when R is 4-pyridinyl or pyrimidinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, wherein the $C_{1-4}$ alkyl group may be substituted with 1-3 fluoro atoms or with a bromo, chloro, iodo, cyano or hydroxy group, $R_1$ represents phenyl or pyridinyl groups, which groups may be substituted with 1-4 substituents Y, which can be the same or different, wherein Y has the above mentioned meaning, or $R_1$ represents pyrimidinyl, pyrazinyl, pyridazinyl or triazinyl, which groups may be substituted with 1-2 substituents Y, which can be the same or different, or $R_1$ represents naphtyl, $R_2$ represents H, branched or unbranched $C_{1-8}$ alkyl, $C_{3-8}$ cycloalkyl, $C_{3-8}$ alkenyl, or $C_{5-8}$ cycloalkenyl, which groups may contain a sulfur, oxygen or nitrogen atom, $R_3$ represents branched or unbranched $C_{2-8}$ alkyl, $C_{1-8}$ alkoxy, $C_{5-8}$ cycloalkyloxy, $C_{3-8}$ cycloalkyl, $C_{5-10}$ bicycloalkyl, $C_{6-10}$ tricycloalkyl, $C_{3-8}$ alkenyl, or $C_{5-8}$ cycloalkenyl, which groups may optionally contain one or more heteroatoms chosen from the group (O, N, S) and which groups may be substituted with a hydroxyl group or 1-2 $C_{1-3}$ alkyl groups or 1-3 fluoro atoms, or $R_3$ represents a benzyl or phenethyl group, which aromatic rings may be substituted with 1-5 substituents Z, which can be the same or different, and chosen from the group $C_{1-3}$-alkyl or alkoxy, hydroxyl, halogen, trifluoromethyl, trifluoromethylthio, trifluoromethoxy, nitro, amino, mono- or dialkyl ($C_{1-2}$)-amino, mono- or dialkyl ($C_{1-2}$)-amido, ($C_{1-3}$)-alkylsulfonyl, dimethyl-sulfamido, $C_{1-3}$ alkoxycarbonyl, carboxyl, trifluoromethylsulfonyl, cyano, carbamoyl, sulfamoyl and acetyl, or $R_3$ represents a phenyl or pyridinyl group, which groups are substituted with 1-4 substituents Z, wherein Z has the meaning as indicated above, with the proviso that when the phenyl or pyridinyl groups are unsubstituted, $R_4$ represents a halogen atom or a cyano, carbamoyl, formyl, acetyl, trifluoroacetyl, fluoroacetyl, propionyl, sulfamoyl, methanesulfonyl, methylsulfanyl or $C_{1-4}$ alkyl group, which $C_{1-4}$ alkyl group may be substituted with 1-3 fluoro atoms or with a bromo, chloro, iodo, cyano or hydroxyl group, or $R_3$ represents a group $NR_5R_6$, with the proviso that $R_2$ represents a hydrogen atom or a methyl group, wherein $R_5$ and $R_6$ are the same or different and represent branched or unbranched $C_{1-4}$ alkyl, or $R_5$ and $R_6$, together with the nitrogen atom to which they are bonded, form a saturated or unsaturated, monocyclic or bicyclic heterocyclic group having 4 to 10 ring atoms which heterocyclic group contains one or two heteroatoms chosen from the group (N, O, S), which heteroatoms can be the same or different, which heterocyclic group may be substituted with a $C_{1-3}$ alkyl group or a hydroxyl group, or $R_2$ and $R_3$, together with the nitrogen atom to which they are bonded, form a saturated or unsaturated heterocyclic group having 4 to 10 ring atoms which heterocyclic group contains one or two heteroatoms chosen from the group (N, O, S), which heteroatoms can be the same or different, and which heterocyclic group may be substituted with a $C_{1-3}$ alkyl group or a hydroxyl group, $R_4$ represents a hydrogen or halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, which $C_{1-4}$ alkyl group may be substituted with 1-3 fluoro atoms or with a bromo, chloro, iodo, cyano or a hydroxyl group, with the proviso that when R, $R_1$, and $R_3$ are phenyl, and $R_2$ is hydrogen, $R_4$ is not a methyl group;

with the proviso that when R is phenyl substituted with chloro, $R_1$ and $R_3$ are phenyl, and $R_2$ is hydrogen, $R_4$ is not a methyl group; and with the proviso that when R is phenyl substituted with methoxy, $R_1$ and $R_3$ are phenyl, and $R_2$ is hydrogen, $R_4$ is not a methyl group;

with the proviso that when R is phenyl substituted with chloro, $R_1$ is phenyl substituted with methoxy, $R_2$ is hydrogen, and $R_3$ is phenyl, $R_4$ is not a methyl group, the process comprising reacting a compound having formula (II), (III) or (IV)

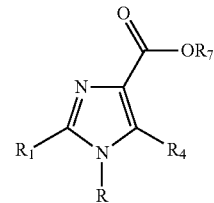

wherein $R_7$ represents a branched or unbranched $C_1$-$C_4$ alkyl group or a benzyl group;

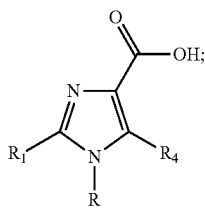

(III)

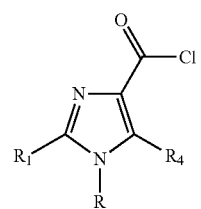

(IV)

with a compound of formula R₂R₃NH.

5. A method for treating at least one disorder involving cannabinoid neurotransmission in a patient in need thereof, comprising:
    administering to the patient a pharmacologically effective amount of at least one compound as claimed in claim 1, wherein the at least one disorder involving cannabinoid neurotransmission is chosen from dementia, obesity, and addiction.

6. A compound as claimed in claim 1, wherein the compound is chosen from:
    1-(4-chlorophenyl)-2-(2,4-dichlorophenyl)-N-(piperidin-1-yl)-1H-imidazole-4-carboxamide,
    1-(4-Chlorophenyl)-2-(2,4-dichlorophenyl)-N-(pyrrolidin-1-yl)-1H-imidazole-4-carboxamide,
    N-(t-Butoxy)-1-(4-chlorophenyl)-2-(2,4-dichlorophenyl)-1H-imidazole-4-carboxamide,
    1-(4-Chlorophenyl)-2-(2,4-dichlorophenyl)-N-phenyl-1H-imidazole-4-carboxamide,
    1-(4-Chlorophenyl)-N-cyclohexyl-2-(2,4-dichlorophenyl)-1H-imidazole-4-carboxamide,
    N-(Benzyl)-1-(4-chlorophenyl)-2-(2,4-dichlorophenyl)-N-methyl-1H-imidazole-4-carboxamide,
    1-[1-(4-Chlorophenyl)-2-(2,4-dichlorophenyl)-4-(1H-imidazolyl)carbonyl]hexahydro-1H-azepine
    2-(4-Chlorophenyl)-1-(2,4-dichlorophenyl)-N-(piperidin-1-yl)-1H-imidazole-4-carboxamide,
    N-(t-Butoxy)-2-(4-chlorophenyl)-1-(2,4-dichlorophenyl)-1H-imidazole-4-carboxamide,
    2-(4-chlorophenyl)-1-(2,4-dichlorophenyl)-5-methyl-N-(piperidin-1-yl)-1H-imidazole-4-carboxamide,
    N-(t-Butoxy)-2-(4-chlorophenyl)-1-(2,4-dichlorophenyl)-5-methyl-1H-imidazole-4-carboxamide,
    1-(4-Chlorophenyl)-2-(2,4-dichlorophenyl)-5-methyl-N-(piperidin-1-yl)-1H-imidazole-4-carboxamide,
    N-(t-Butoxy)-2-(2,4-dichlorophenyl)-1-(4-chlorophenyl)-5-methyl-1H-imidazole-4-carboxamide,
    N-(t-Butoxy)-1-(4-chlorophenyl)-2-(2,4-dichlorophenyl)-5-ethyl-1H-imidazole-4-carboxamide,
    1-(4-Chlorophenyl)-2-(2,4-dichlorophenyl)-5-ethyl-N-(piperidin-1-yl)-1H-imidazole-4-carboxamide,
    1-(4-Bromophenyl)-N-(t-butoxy)-2-(2,4-dichlorophenyl)-5-methyl-1H-imidazole-4-carboxamide,
    1-(4-Bromophenyl)-2-(2,4-dichlorophenyl)-5-methyl-N-(piperidin-1-yl)-1H-imidazole-4-carboxamide,
    1-(4-Bromophenyl)-N-(t-butoxy)-2-(2,4-dichlorophenyl)-5-ethyl-1H-imidazole-4-carboxamide,
    1-(4-Bromophenyl)-2-(2,4-dichlorophenyl)-5-ethyl-N-(piperidin-1-yl)-1H-imidazole-4-carboxamide,
    1-(4-Bromophenyl)-N-cyclohexyl-2-(2,4-dichlorophenyl)-5-ethyl-1H-imidazole-4-carboxamide,
    1-(4-Bromophenyl)-2-(2,4-dichlorophenyl)-5-ethyl-N-(n-pentyl)-1H-imidazole-4-carboxamide,
    1-(4-bromophenyl)-2-(2,4-dichlorophenyl)-N-(piperidin-1-yl)-1H-imidazole-4-carboxamide,
    N-(t-Butoxy)-1-(4-bromophenyl)-2-(2,4-dichlorophenyl)-1H-imidazole-4-carboxamide,
    1-(4-Bromophenyl)-2-(2,4-dichlorophenyl)-N-(pyrrolidin-1-yl)-1H-imidazole-4-carboxamide,
    N-(Azepan-1-yl)-1-(4-bromophenyl)-2-(2,4-dichlorophenyl)-1H-imidazole-4-carboxamide,
    1-(4-Chlorophenyl)-2-(2,4-dichlorophenyl)-N-(hexahydrocyclopenta[c]pyrrol-2(1H)-yl)-1H-imidazole-4-carboxamide,
    1-(4-Chlorophenyl)-2-(2,4-dichlorophenyl)-N-(4-fluorobenzyl)-1H-imidazole-4-carboxamide,
    1-(4-Chlorophenyl)-2-(2-methoxy-4-chlorophenyl)-N-(piperidin-1-yl)-1H-imidazole-4-carboxamide,
    1-(4-Chlorophenyl)-N-cyclohexyl-2-(2-methoxy-4-chlorophenyl)-1H-imidazole-4-carboxamide,
    1-(4-Chlorophenyl)-2-(2-fluoro-4-chlorophenyl)-N-(piperidin-1-yl)-1H-imidazole-4-carboxamide,
    2-(2,4-Dichlorophenyl)-1-(4-fluorophenyl)-N-(piperidin-1-yl)-1H-imidazole-4-carboxamide,
    N-Cyclohexyl-2-(2,4-dichlorophenyl)-1-(4-fluorophenyl)-1H-imidazole-4-carboxamide,
    N-Cyclohexyl-2-(2-fluoro-4-chlorophenyl)-1-(4-chlorophenyl)-1H-imidazole-4-carboxamide,
    1-(4-Chlorophenyl)-2-(2-methoxy-4-chlorophenyl)-N-(n-pentyl)-1H-imidazole-4-carboxamide,
    2-(2,4-Dichlorophenyl)-1-(4-methoxyphenyl)-N-(piperidin-1-yl)-1H-imidazole-4-carboxamide,
    N-Cyclohexyl-2-(2,4-dichlorophenyl)-1-(4-methoxyphenyl)-1H-imidazole-4-carboxamide,
    1-(4-Chlorophenyl)-2-(2,4-dichlorophenyl)-N,N-diethyl-1H-imidazole-4-carboxamide,
    1-(4-Chlorophenyl)-N-cyclohexyl-2-(2-trifluoromethyl-4-chlorophenyl)-1H-imidazole-4-carboxamide,
    1-(4-Chlorophenyl)-N-(piperidin-1-yl)-2-(2-trifluoromethyl-4-chlorophenyl)-1H-imidazole-4-carboxamide,
    N-(1-Adamantyl)-1-(4-chlorophenyl)-2-(2-trifluoromethyl-4-chlorophenyl)-1H-imidazole-4-carboxamide,
    1-(4-Chlorophenyl)-N-(2,2,2-trifluoroethyl)-2-(2-trifluoromethyl-4-chlorophenyl)-1H-imidazole-4-carboxamide,
    2-(2,4-Dichlorophenyl)-1-(pyridin-3-yl)-N-(piperidin-1-yl)-1H-imidazole-4-carboxamide,
    N-Cyclohexyl-2-(2,4-dichlorophenyl)-1-(pyridin-3-yl)-1H-imidazole-4-carboxamide,
    2-(2,4-Dichlorophenyl)-1-(pyridin-3-yl)-N-(n-pentyl)-1H-imidazole-4-carboxamide,
    2-(2,4-dichlorophenyl)-5-methyl-N-(piperidin-1-yl)-1-(4-(trifluoromethyl)phenyl)-1H-imidazole-4-carboxamide,
    2-(2,4-dichlorophenyl)-N-(piperidin-1-yl)-1-(4-(trifluoromethyl)phenyl)-1H-imidazole-4-carboxamide,
    N-Cyclohexyl-2-(2,4-dichlorophenyl)-5-methyl-1-(4-(trifluoromethyl)phenyl)-1H-imidazole-4-carboxamide,
    N-Cyclohexyl-2-(2,4-dichlorophenyl)-1-(4-(trifluoromethyl)phenyl)-1H-imidazole-4-carboxamide, N-(1-cyclohexyl)-2-(2,4-dichlorophenyl)-5-methyl-1-(4-methoxyphenyl)-1H-imidazole-4-carboxamide, 1-(4-Chlorophenyl)-2-(2,4-dichlorophenyl)-N,N,5-trimethyl-1H-imidazole-4-carboxamide, 1-(4-Chloropyridin-2-yl)-2-(2,4-dichlorophenyl)-5-methyl-N-(piperidin-1-yl)-1H-imidazole-4-carboxamide, 1-(4-Chloropyridin-2-yl)-2-(2,4-dichlorophenyl)-5-methyl-N-(4-morpholinyl)-1H-imidazole-4-carboxamide, N-(1-Azepanyl)-1-(4-Chloropyridin-2-yl)-2-(2,4-dichlorophenyl)-5-methyl-1H-imidazole-4-carboxamide, 1-(4-Chloropyridin-2-yl)-N-cyclohexyl-2-(2,4-dichlorophenyl)-5-methyl-1H-imidazole-4-carboxamide, 1-(4-Chloropyridin-2-yl)-2-(2,4-dichlorophenyl)-5-methyl-N-(n-pentyl)-1H-imidazole-4-carboxamide, 1-(4-Chloropyridin-2-yl)-2-(2,4-dichlorophenyl)-N-(4-fluorobenzyl)-5-methyl-1H-imidazole-4-carboxamide, 1-(4-Chlorophenyl)-N-cyclohexyl-5-methyl-2-(2-trifluoromethyl-4-chlorophenyl)-1H-imidazole-4-carboxamide, 1-(4-Chlorophenyl)-5-methyl-N-(piperidin-1-yl)-2-(2-trifluoromethyl-4-chlorophenyl)-1H-imidazole-4-carboxamide, 1-(4-Chlorophenyl)-2-(2-methoxy-4-chlorophenyl)-5-methyl-N-(n-pentyl)-1H-imidazole-4-carboxamide, 1-(4-Chlorophenyl)-2-(2-methoxy-4-chlorophenyl)-5-methyl-N-(piperidin-1-yl)-1H-imidazole-4-carboxamide, N-Cyclohexyl-1-(4-chlorophenyl)-2-(2-methoxy-4-chlorophenyl)-5-methyl-1H-imidazole-4-carboxamide, 2-(2,4-Dichlorophenyl)-1-(4-fluorophenyl)-5-methyl-N-(piperidin-1-yl)-1H-imidazole-4-carboxamide, 2-(2,4-Dichlorophenyl)-5-methyl-1-(4-methoxyphenyl)-N-(piperidin-1-yl)-1H-imidazole-4-carboxamide, N-Cyclohexyl-1-(4-fluorophenyl)-2-(2,4-dichlorophenyl)-5-methyl-1H-imidazole-4-carboxamide, 1-(4-Chlorophenyl)-5-methyl-N-(n-pentyl)-2-(2-trifluoromethyl-4-chlorophenyl)-1H-imidazole-4-carboxamide, 1-(4-Chlorophenyl)-2-(2-fluoro-4-chlorophenyl)-5-methyl-N-(piperidin-1-yl)-1H-imidazole-4-carboxamide, 1-(4-Chlorophenyl)-2-(2-fluoro-4-chlorophenyl)-5-methyl-N-(n-pentyl)-1H-imidazole-4-carboxamide, 1-(4-Chlorophenyl)-N-(cyclohexyl)-2-(2-fluoro-4-chlorophenyl)-5-methyl-1H-imidazole-4-carboxamide, 1-(4-Chlorophenyl)-N-(cyclohexyl)-2-(1,5-dimethyl-1H-pyrrol-2-yl)-5-methyl-1H-imidazole-4-carboxamide, 1-(4-Chlorophenyl)-2-(1,5-dimethyl-1H-pyrrol-2-yl)-5-methyl-N-(piperidin-1-yl)-1H-imidazole-4-carboxamide, 2-(2-Chlorophenyl)-1-(3-fluorophenyl)-5-methyl-N-(piperidin-1-yl)-1H-imidazole-4-carboxamide, 2-(2-Chlorophenyl)-1-(3-fluorophenyl)-5-methyl-N-(n-pentyl)-1H-imidazole-4-carboxamide, 2-(2-Chlorophenyl)-N-cyclohexyl-1-(3-fluorophenyl)-5-methyl-1H-imidazole-4-carboxamide, 2-(2-Chlorophenyl)-1-(3-fluorophenyl)-N-(2-(4-fluorophenyl)ethyl)-5-methyl-1H-imidazole-4-carboxamide, 1-(4-Chloropyridin-2-yl)-2-(2,4-dichlorophenyl)-5-ethyl-N-(piperidin-1-yl)-1H-imidazole-4-carboxamide, 1-(4-Chloropyridin-2-yl)-2-(2,4-dichlorophenyl)-5-ethyl-N-(4-morpholinyl)-1H-imidazole-4-carboxamide, N-(1-Azepanyl)-1-(4-Chloropyridin-2-yl)-2-(2,4-dichlorophenyl)-5-ethyl-1H-imidazole-4-carboxamide, 1-(4-Chloropyridin-2-yl)-N-cyclohexyl-2-(2,4-dichlorophenyl)-5-ethyl-1H-imidazole-4-carboxamide, 1-(4-Chloropyridin-2-yl)-2-(2,4-dichlorophenyl)-5-ethyl-N-(n-pentyl)-1H-imidazole-4-carboxamide, 1-(4-Chloropyridin-2-yl)-2-(2,4-dichlorophenyl)-5-ethyl-N-(4-fluorophenylmethyl)-1H-imidazole-4-carboxamide, 1-(4-Chlorophenyl)-2-(2,4-dichlorophenyl)-N-(hexahydrocyclopenta-[c]pyrrol-2(1H)-yl)-5-methyl-1H-imidazole-4-carboxamide, 1-(4-Chlorophenyl)-2-(2,4-dichlorophenyl)-5-methyl-N-phenyl-1H-imidazole-4-carboxamide, 1-(4-Chlorophenyl)-2-(2,4-dichlorophenyl)-5-methyl-N-(tetrahydro-2H-pyran-2-yloxy)-1H-imidazole-4-carboxamide, N-(Exo-bicyclo[2.2.1]hept-2-yl)-1-(4-chlorophenyl)-2-(2,4-dichlorophenyl)-5-methyl-1H-imidazole-4-carboxamide, 1-(4-Chlorophenyl)-2-(2,4-dichlorophenyl)-N-(2-fluoroethyl)-5-methyl-1H-imidazole-4-carboxamide, 1-(4-Chlorophenyl)-2-(2,4-dichlorophenyl)-N-(trans-4-hydroxycyclohexyl)-5-methyl-1H-imidazole-4-carboxamide, 1-{[1-(4-Chlorophenyl)-2-(2,4-dichlorophenyl)-5-methyl-1H-imidazol-4-yl]carbonyl}-4-hydroxypiperidine 1-{[1-(4-Chlorophenyl)-2-(2,4-dichlorophenyl)-5-methyl-1H-imidazol-4-yl]carbonyl}-1,2,3,4-tetrahydroisoquinoline N-(Endo-bicyclo[2.2.1]hept-2-yl)-1-(4-chlorophenyl)-2-(2,4-dichlorophenyl)-5-methyl-1H-imidazole-4-carboxamide, 1-(4-Chlorophenyl)-2-(2,4-dichlorophenyl)-N-(4-fluorobenzyl)-5-methyl-1H-imidazole-4-carboxamide, 1-(4-Chlorophenyl)-2-(2,4-dichlorophenyl)-5-methyl-N-(n-pentyl)-1H-imidazole-4-carboxamide, N-(Azepan-1-yl)-1-(4-chlorophenyl)-2-(2,4-dichlorophenyl)-5-methyl-1H-imidazole-4-carboxamide, 1-(4-Chlorophenyl)-2-(2,4-dichlorophenyl)-5-methyl-N-(pyrrolidin-1-yl)-1H-imidazole-4-carboxamide, 1-(4-Chlorophenyl)-2-(2,4-dichlorophenyl)-5-methyl-N-(morpholin-4-yl)-1H-imidazole-4-carboxamide, 2-(2,5-Dichlorophenyl)-5-methyl-1-phenyl-N-(piperidin-1-yl)-1H-imidazole-4-carboxamide, N-Cyclohexyl-2-(2,5-dichlorophenyl)-5-methyl-1-phenyl-1H-imidazole-4-carboxamide, N-Cyclohexyl-2-(2,4-dichlorophenyl)-1-(2,5-difluorophenyl)-5-ethyl-1H-imidazole-4-carboxamide, N-Cyclohexyl-2-(2,4-dichlorophenyl)-1-(2,5-difluorophenyl)-5-methyl-1H-imidazole-4-carboxamide, N-Cyclohexyl-2-(1,5-dimethyl-1H-pyrrol-2-yl)-5-ethyl-1-phenyl-1H-imidazole-4-carboxamide, N-Cyclohexyl-2-(2,5-dichlorophenyl)-5-ethyl-1-phenyl-1H-imidazole-4-carboxamide, 2-(2,5-Dichlorophenyl)-5-ethyl-1-phenyl-N-(piperidin-1-yl)-1H-imidazole-4-carboxamide, 1-(4-Chlorophenyl)-5-methyl-2-(3-methylpyridin-2-yl)-N-(piperidin-1-yl)-1H-imidazole-4-carboxamide, 1-(4-Chlorophenyl)-N-cyclohexyl-5-methyl-2-(3-methylpyridin-2-yl)-1H-imidazole-4-carboxamide, 1-(4-Chlorophenyl)-2-(2,4-dichlorophenyl)-5-methyl-N-(3-(trifluoromethyl)phenyl)-1H-imidazole-4-carboxamide, 1-(4-Chlorophenyl)-2-(2,4-dichlorophenyl)-5-methyl-N-(3-(trifluoromethyl)benzyl)-1H-imidazole-4-carboxamide, 1-(4-Chlorophenyl)-2-(2,4-dichlorophenyl)-5-methyl-N-(4-(trifluoromethyl)benzyl)-1H-imidazole-4-carboxamide, 1-(4-Chlorophenyl)-N-cyclopentyl-2-(2,4-dichlorophenyl)-5-methyl-1H-imidazole-4-carboxamide,
1-(4-Chlorophenyl)-N-cycloheptyl-2-(2,4-dichlorophenyl)-5-methyl-1H-imidazole-4-carboxamide,
1-(4-bromophenyl)-5-chloro-2-(2,4-dichloro-phenyl)-N-(piperidin-1-yl)-1H-imidazole-4-carboxamide,
1-(4-chlorophenyl)-5-cyano-2-(2,4-dichlorophenyl)-N-(piperidin-1-yl)-1H-imidazole-4-carboxamide,
1-(4-Chlorophenyl)-2-(2,4-dichlorophenyl)-5-iodo-N-(piperidin-1-yl)-1H-imidazole-4-carboxamide,
1-(4-Chlorophenyl)-N-cyclohexyl-2-(2,4-dichlorophenyl)-5-iodo-1H-imidazole-4-carboxamide, and
1-(4-Chlorophenyl)-5-cyano-N-cyclohexyl-2-(2,4-dichlorophenyl)-1H-imidazole-4-carboxamide, and salts thereof.

* * * * *